(12) United States Patent
Li et al.

(10) Patent No.: US 11,787,852 B2
(45) Date of Patent: Oct. 17, 2023

(54) RECOMBINANT HUMAN TYPE XVII COLLAGEN, AND PREPARATION METHOD AND USE THEREOF

(71) Applicant: JIANGSU TRAUTEC MEDICAL TECHNOLOGY CO., LTD., Changzhou (CN)

(72) Inventors: Jiajia Li, Changzhou (CN); Liping Wang, Changzhou (CN); Song Qian, Changzhou (CN)

(73) Assignee: JIANGSU TRAUTEC MEDICAL TECHNOLOGY CO., LTD., Changzhou (CN)

( * ) Notice: Subject to any disclaimer, the term of this patent is extended or adjusted under 35 U.S.C. 154(b) by 0 days.

(21) Appl. No.: 17/908,258

(22) PCT Filed: Jan. 14, 2022

(86) PCT No.: PCT/CN2022/071968
§ 371 (c)(1),
(2) Date: Aug. 31, 2022

(87) PCT Pub. No.: WO2022/237224
PCT Pub. Date: Nov. 17, 2022

(65) Prior Publication Data
US 2023/0119018 A1    Apr. 20, 2023

(30) Foreign Application Priority Data

May 13, 2021   (CN) .......................... 202110520499.9

(51) Int. Cl.
| C07K 14/78 | (2006.01) |
| A61P 17/02 | (2006.01) |
| C12N 15/81 | (2006.01) |

(52) U.S. Cl.
CPC .............. C07K 14/78 (2013.01); A61P 17/02 (2018.01); C12N 15/81 (2013.01)

(58) Field of Classification Search
CPC .......... C07K 14/78; A61P 17/02; C12N 15/81
See application file for complete search history.

(56) References Cited

FOREIGN PATENT DOCUMENTS

| CN | 110029111 A | 7/2019 | |
| CN | 110845603 A | 2/2020 | |
| CN | 113185604 A | 7/2021 | |
| WO | 9738710 A1 | 10/1997 | |
| WO | 03087343 A1 | 10/2003 | |
| WO | WO 2020/227642 * | 11/2020 | ............. A61K 38/17 |

OTHER PUBLICATIONS

Hee-Seok Jeong, et al., Isolation and Characterization of Collagen from Marine Fish (*Thunnus obesus*), Biotechnology and Bioprocess Engineering, 2013, pp. 1185-1191, vol. 18.
Chen Jingtao, et al., FT-IR Spectrometr ic Study of Reconbinant Collagen and Bor ine Tendon Type I Colleagen, Material Guide, 2008, pp. 119-121.
Barbara Brodsky Doyle, et al., Infrared Spectroscopy of Collagen and Collagen-Like Polypeptides, Biopolymers, 1975, pp. 937-957, vol. 14.
Zhou Ai-Mei, et al., Purification and characterization of recombinant human-source collagen, Food and Fermentation Industries, 2015, pp. 46-52, vol. 41 No. 3.
Juming Yao, et al., Design, Expression and Characterization of Collagen-Like Proteins Based on the Cell Adhesive and Crosslinking Sequences Derived from Native Collagens, Journal of Biochemistry, 2004, pp. 643-649, vol. 136.
Ana Victoria Ponce Bobadilla, et al., In vitro cell migration quantification method for scratch assays, Interface, 2019, pp. 1-11, vol. 16.
Tong Liu, Full-thickness Skin Defect Reconstruction in Rats Using Minced Split-thickness Skin Grafts with Recombinant Human Collagen Hydrogel or Artificial Dermal Overlay: an Experimental Study, Naval Medical University Master Thesis, 2019.
Jicheng Li, Histology and Embryology Experiments Laboratory Guide, National Health Commission's "Thirteenth Five-Year Plan" textbook supporting textbooks, 2018.
Q9UMD9-1 sequence, Q9UMD9-COHA1_HUMAN, Retrived from: https://www.uniprot.org/uniprotkb/Q9UMD9.
UniProtKB/Swiss-Prot: Q9UMD9.3, RecName: Full=Collagen alpha-1(XVII) chain; AltName: Full=180 kDa bullous pemphigoid antigen 2; AltName: Full=Bullous pemphigoid antigen 2; Contains: RecName: Full=120 kDa linear IgA disease antigen; AltName: Full=120 kDa linear IgA dermatosis antigen; AltName: Full=Linear IgA disease antigen 1; Short=LAD-1; Contains: RecName: Full=97 kDa linear IgA disease antigen; AltName: Full=97 kDa linear IgA bullous dermatosis antigen; Short=97 kDa LAD antigen; Short=97-LAD; AltName: Full=Linear IgA bullous disease antigen of UniProt, Q9UMD9-COHA1_Human, retrieved Sep. 16, 2022, 8 pages.

* cited by examiner

*Primary Examiner* — Amber D Steele
(74) *Attorney, Agent, or Firm* — Bayramoglu Law Offices LLC

(57) ABSTRACT

A recombinant human type XVII collagen consists of an amino acid sequence shown in $(A)_n$ or includes the amino acid sequence shown in $(A)_n$, where A is a sequence set forth in SEQ ID NO: 2, a sequence undergoing an amino acid modification to a predetermined extent based on SEQ ID NO: 2, or a sequence that has more than 80% homology with SEQ ID NO: 2; n is an integer greater than or equal to 1; and A represents a basic unit, and when there are two or more basic units, the two or more basic units are identical or different and are directly connected in tandem through a peptide bond. In the present disclosure, it is confirmed that the recombinant human type XVII collagen can undergo efficient secretory and soluble expression in eukaryotic host cells such as *Pichia pastoris* (*P. pastoris*).

30 Claims, 11 Drawing Sheets

Specification includes a Sequence Listing.

sequence alignment with the native human type XVII collagen shown in SEQ ID NO: 1

FIG. 9 sequence alignment with the native human type XVII collagen shown in SEQ ID NO: 1

FIG. 10

SEQUENCE LISTING

<160> NUMBER OF SEQ ID NOS: 10

<210> SEQ ID NO 1

<211> LENGTH: 1497
<212> TYPE: PRT
<213> ORGANISM: Homo sapiens

<400> SEQUENCE: 1

```
Met Asp Val Thr Lys Lys Asn Lys Arg Asp Gly Thr Glu Val Thr Glu
1               5                   10                  15

Arg Ile Val Thr Glu Thr Val Thr Thr Arg Leu Thr Ser Leu Pro Pro
            20                  25                  30

Lys Gly Gly Thr Ser Asn Gly Tyr Ala Lys Thr Ala Ser Leu Gly Gly
        35                  40                  45

Gly Ser Arg Leu Glu Lys Gln Ser Leu Thr His Gly Ser Ser Gly Tyr
    50                  55                  60

Ile Asn Ser Thr Gly Ser Thr Arg Gly His Ala Ser Thr Ser Ser Tyr
65                  70                  75                  80

Arg Arg Ala His Ser Pro Ala Ser Thr Leu Pro Asn Ser Pro Gly Ser
                85                  90                  95

Thr Phe Glu Arg Lys Thr His Val Thr Arg His Ala Tyr Glu Gly Ser
            100                 105                 110

Ser Ser Gly Asn Ser Ser Pro Glu Tyr Pro Arg Lys Glu Phe Ala Ser
        115                 120                 125

Ser Ser Thr Arg Gly Arg Ser Gln Thr Arg Glu Ser Glu Ile Arg Val
    130                 135                 140

Arg Leu Gln Ser Ala Ser Pro Ser Thr Arg Trp Thr Glu Leu Asp Asp
145                 150                 155                 160

Val Lys Arg Leu Leu Lys Gly Ser Arg Ser Ala Ser Val Ser Pro Thr
                165                 170                 175

Arg Asn Ser Ser Asn Thr Leu Pro Ile Pro Lys Lys Gly Thr Val Glu
            180                 185                 190

Thr Lys Ile Val Thr Ala Ser Ser Gln Ser Val Ser Gly Thr Tyr Asp
        195                 200                 205

Ala Thr Ile Leu Asp Ala Asn Leu Pro Ser His Val Trp Ser Ser Thr
    210                 215                 220

Leu Pro Ala Gly Ser Ser Met Gly Thr Tyr His Asn Asn Met Thr Thr
225                 230                 235                 240

Gln Ser Ser Ser Leu Leu Asn Thr Asn Ala Tyr Ser Ala Gly Ser Val
                245                 250                 255

Phe Gly Val Pro Asn Asn Met Ala Ser Cys Ser Pro Thr Leu His Pro
            260                 265                 270

Gly Leu Ser Thr Ser Ser Ser Val Phe Gly Met Gln Asn Asn Leu Ala
        275                 280                 285

Pro Ser Leu Thr Thr Leu Ser His Gly Thr Thr Thr Ser Thr Ala
    290                 295                 300

Tyr Gly Val Lys Lys Asn Met Pro Gln Ser Pro Ala Ala Val Asn Thr
305                 310                 315                 320

Gly Val Ser Thr Ser Ala Ala Cys Thr Thr Ser Val Gln Ser Asp Asp
                325                 330                 335

Leu Leu His Lys Asp Cys Lys Phe Leu Ile Leu Glu Lys Asp Asn Thr
            340                 345                 350

Pro Ala Lys Lys Glu Met Glu Leu Leu Ile Met Thr Lys Asp Ser Gly
        355                 360                 365

Lys Val Phe Thr Ala Ser Pro Ala Ser Ile Ala Ala Thr Ser Phe Ser
    370                 375                 380

Glu Asp Thr Leu Lys Lys Glu Lys Gln Ala Ala Tyr Asn Ala Asp Ser
```

```
                385                 390                 395                 400
Gly Leu Lys Ala Glu Ala Asn Gly Asp Leu Lys Thr Val Ser Thr Lys
                    405                 410                 415
Gly Lys Thr Thr Thr Ala Asp Ile His Ser Tyr Gly Ser Ser Gly Gly
            420                 425                 430
Gly Gly Ser Gly Gly Gly Gly Val Gly Gly Ala Gly Gly Gly Gly Pro
                435                 440                 445
Trp Gly Pro Ala Pro Ala Trp Cys Pro Cys Gly Ser Cys Cys Ser Trp
            450                 455                 460
Trp Lys Trp Leu Leu Gly Leu Leu Thr Trp Leu Leu Leu Leu Leu Gly
465                 470                 475                 480
Leu Leu Phe Gly Leu Ile Ala Leu Ala Glu Glu Val Arg Lys Leu Lys
                485                 490                 495
Ala Arg Val Asp Glu Leu Glu Arg Ile Arg Arg Ser Ile Leu Pro Tyr
            500                 505                 510
Gly Asp Ser Met Asp Arg Ile Glu Lys Asp Arg Leu Gln Gly Met Ala
                515                 520                 525
Pro Ala Ala Gly Ala Asp Leu Asp Lys Ile Gly Leu His Ser Asp Ser
            530                 535                 540
Gln Glu Glu Leu Trp Met Phe Val Arg Lys Lys Leu Met Met Glu Gln
545                 550                 555                 560
Glu Asn Gly Asn Leu Arg Gly Ser Pro Gly Pro Lys Gly Asp Met Gly
                565                 570                 575
Ser Pro Gly Pro Lys Gly Asp Arg Gly Phe Pro Gly Thr Pro Gly Ile
            580                 585                 590
Pro Gly Pro Leu Gly His Pro Gly Pro Gln Gly Pro Lys Gly Gln Lys
            595                 600                 605
Gly Ser Val Gly Asp Pro Gly Met Glu Gly Pro Met Gly Gln Arg Gly
        610                 615                 620
Arg Glu Gly Pro Met Gly Pro Arg Gly Glu Ala Gly Pro Pro Gly Ser
625                 630                 635                 640
Gly Glu Lys Gly Glu Arg Gly Ala Ala Gly Glu Pro Gly Pro His Gly
                645                 650                 655
Pro Pro Gly Val Pro Gly Ser Val Gly Pro Lys Gly Ser Ser Gly Ser
            660                 665                 670
Pro Gly Pro Gln Gly Pro Pro Gly Pro Val Gly Leu Gln Gly Leu Arg
            675                 680                 685
Gly Glu Val Gly Leu Pro Gly Val Lys Gly Asp Lys Gly Pro Met Gly
        690                 695                 700
Pro Pro Gly Pro Lys Gly Asp Gln Gly Glu Lys Gly Pro Arg Gly Leu
705                 710                 715                 720
Thr Gly Glu Pro Gly Met Arg Gly Leu Pro Gly Ala Val Gly Glu Pro
                725                 730                 735
Gly Ala Lys Gly Ala Met Gly Pro Ala Gly Pro Asp Gly His Gln Gly
            740                 745                 750
Pro Arg Gly Glu Gln Gly Leu Thr Gly Met Pro Gly Ile Arg Gly Pro
            755                 760                 765
Pro Gly Pro Ser Gly Asp Pro Gly Lys Pro Gly Leu Thr Gly Pro Gln
            770                 775                 780
Gly Pro Gln Gly Leu Pro Gly Thr Pro Gly Arg Pro Gly Ile Lys Gly
785                 790                 795                 800
Glu Pro Gly Ala Pro Gly Lys Ile Val Thr Ser Glu Gly Ser Ser Met
                805                 810                 815
```

```
Leu Thr Val Pro Gly Pro Pro Gly Pro Pro Gly Ala Met Gly Pro Pro
            820                 825                 830

Gly Pro Pro Gly Ala Pro Gly Pro Ala Gly Pro Ala Gly Leu Pro Gly
            835                 840                 845

His Gln Glu Val Leu Asn Leu Gln Gly Pro Pro Gly Pro Pro Gly Pro
            850                 855                 860

Arg Gly Pro Pro Gly Pro Ser Ile Pro Gly Pro Pro Gly Pro Arg Gly
865                 870                 875                 880

Pro Pro Gly Glu Gly Leu Pro Gly Pro Pro Gly Pro Pro Gly Ser Phe
                885                 890                 895

Leu Ser Asn Ser Glu Thr Phe Leu Ser Gly Pro Pro Gly Pro Pro Gly
            900                 905                 910

Pro Pro Gly Pro Lys Gly Asp Gln Gly Pro Pro Gly Pro Arg Gly His
            915                 920                 925

Gln Gly Glu Gln Gly Leu Pro Gly Phe Ser Thr Ser Gly Ser Ser Ser
            930                 935                 940

Phe Gly Leu Asn Leu Gln Gly Pro Pro Gly Pro Pro Gly Pro Gln Gly
945                 950                 955                 960

Pro Lys Gly Asp Lys Gly Asp Pro Gly Val Pro Gly Ala Leu Gly Ile
            965                 970                 975

Pro Ser Gly Pro Ser Glu Gly Gly Ser Ser Ser Thr Met Tyr Val Ser
            980                 985                 990

Gly Pro Pro Gly Pro Pro Gly Pro Pro Gly Pro Pro Gly Ser Ile Ser
            995                 1000                1005

Ser Ser Gly Gln Glu Ile Gln Gln Tyr Ile Ser Glu Tyr Met Gln
    1010                1015                1020

Ser Asp Ser Ile Arg Ser Tyr Leu Ser Gly Val Gln Gly Pro Pro
    1025                1030                1035

Gly Pro Pro Gly Pro Pro Gly Pro Val Thr Thr Ile Thr Gly Glu
    1040                1045                1050

Thr Phe Asp Tyr Ser Glu Leu Ala Ser His Val Val Ser Tyr Leu
    1055                1060                1065

Arg Thr Ser Gly Tyr Gly Val Ser Leu Phe Ser Ser Ser Ile Ser
    1070                1075                1080

Ser Glu Asp Ile Leu Ala Val Leu Gln Arg Asp Asp Val Arg Gln
    1085                1090                1095

Tyr Leu Arg Gln Tyr Leu Met Gly Pro Arg Gly Pro Pro Gly Pro
    1100                1105                1110

Pro Gly Ala Ser Gly Asp Gly Ser Leu Leu Ser Leu Asp Tyr Ala
    1115                1120                1125

Glu Leu Ser Ser Arg Ile Leu Ser Tyr Met Ser Ser Ser Gly Ile
    1130                1135                1140

Ser Ile Gly Leu Pro Gly Pro Pro Gly Pro Pro Gly Leu Pro Gly
    1145                1150                1155

Thr Ser Tyr Glu Glu Leu Leu Ser Leu Leu Arg Gly Ser Glu Phe
    1160                1165                1170

Arg Gly Ile Val Gly Pro Pro Gly Pro Pro Gly Pro Pro Gly Ile
    1175                1180                1185

Pro Gly Asn Val Trp Ser Ser Ile Ser Val Glu Asp Leu Ser Ser
    1190                1195                1200

Tyr Leu His Thr Ala Gly Leu Ser Phe Ile Pro Gly Pro Pro Gly
    1205                1210                1215
```

```
Pro Pro  Gly Pro Pro Gly Pro  Arg Gly Pro Pro  Gly Val Ser Gly
    1220             1225              1230

Ala Leu  Ala Thr Tyr Ala Ala  Glu Asn Ser Asp  Ser Phe Arg Ser
    1235             1240              1245

Glu Leu  Ile Ser Tyr Leu Thr  Ser Pro Asp Val  Arg Ser Phe Ile
    1250             1255              1260

Val Gly  Pro Pro Gly Pro Pro  Gly Pro Gln Gly  Pro Pro Gly Asp
    1265             1270              1275

Ser Arg  Leu Leu Ser Thr Asp  Ala Ser His Ser  Arg Gly Ser Ser
    1280             1285              1290

Ser Ser  Ser His Ser Ser Ser  Val Arg Arg Gly  Ser Ser Tyr Ser
    1295             1300              1305

Ser Ser  Met Ser Thr Gly Gly  Gly Gly Ala Gly  Ser Leu Gly Ala
    1310             1315              1320

Gly Gly  Ala Phe Gly Glu Ala  Ala Gly Asp Arg  Gly Pro Tyr Gly
    1325             1330              1335

Thr Asp  Ile Gly Pro Gly Gly  Gly Tyr Gly Ala  Ala Ala Glu Gly
    1340             1345              1350

Gly Met  Tyr Ala Gly Asn Gly  Gly Leu Leu Gly  Ala Asp Phe Ala
    1355             1360              1365

Gly Asp  Leu Asp Tyr Asn Glu  Leu Ala Val Arg  Val Ser Glu Ser
    1370             1375              1380

Met Gln  Arg Gln Gly Leu Leu  Gln Gly Met Ala  Tyr Thr Val Gln
    1385             1390              1395

Gly Pro  Pro Gly Gln Pro Gly  Pro Gln Gly Pro  Pro Gly Ile Ser
    1400             1405              1410

Lys Val  Phe Ser Ala Tyr Ser  Asn Val Thr Ala  Asp Leu Met Asp
    1415             1420              1425

Phe Phe  Gln Thr Tyr Gly Ala  Ile Gln Gly Pro  Pro Gly Gln Lys
    1430             1435              1440

Gly Glu  Met Gly Thr Pro Gly  Pro Lys Gly Asp  Arg Gly Pro Ala
    1445             1450              1455

Gly Pro  Pro Gly His Pro Gly  Pro Pro Gly Pro  Arg Gly His Lys
    1460             1465              1470

Gly Glu  Lys Gly Asp Lys Gly  Asp Gln Val Tyr  Ala Gly Arg Arg
    1475             1480              1485

Arg Arg  Arg Ser Ile Ala Val  Lys Pro
    1490             1495

<210> SEQ ID NO 2
<211> LENGTH: 233
<212> TYPE: PRT
<213> ORGANISM: Artificial Sequence
<220> FEATURE:
<223> OTHER INFORMATION: Recombinant human type XVII collagen 170801

<400> SEQUENCE: 2

Gly Ser Pro Gly Pro Lys Gly Asp Met Gly Ser Pro Gly Pro Lys Gly
1               5                   10                  15

Asp Arg Gly Phe Pro Gly Thr Pro Gly Ile Pro Gly Pro Leu Gly His
                20                  25                  30

Pro Gly Pro Gln Gly Pro Lys Gly Gln Lys Gly Ser Val Gly Asp Pro
            35                  40                  45

Gly Met Glu Gly Pro Gly Glu Lys Gly Glu Arg Gly Ala Ala Gly Glu
        50                  55                  60
```

```
Pro Gly Pro His Gly Pro Pro Gly Val Pro Gly Ser Val Gly Pro Lys
65                  70                  75                  80

Gly Ser Ser Gly Ser Pro Gly Pro Gln Gly Pro Pro Gly Pro Val Gly
                85                  90                  95

Leu Gln Gly Leu Arg Gly Glu Val Gly Leu Pro Gly Val Lys Gly Asp
            100                 105                 110

Lys Gly Pro Met Gly Pro Pro Gly Pro Lys Gly Asp Gln Gly Glu Lys
        115                 120                 125

Gly Pro Pro Gly Pro Pro Gly Pro Pro Gly Pro Lys Gly Asp Gln Gly
    130                 135                 140

Pro Pro Gly Pro Arg Gly His Gln Gly Glu Gln Gly Leu Pro Gly Phe
145                 150                 155                 160

Ser Gly Pro Pro Gly Pro Pro Gly Pro Gln Gly Pro Lys Gly Asp Lys
                165                 170                 175

Gly Asp Pro Gly Val Pro Gly Ala Leu Gly Ile Pro Gly Pro Pro Gly
            180                 185                 190

Gln Lys Gly Glu Met Gly Thr Pro Gly Pro Lys Gly Asp Arg Gly Pro
        195                 200                 205

Ala Gly Pro Pro Gly His Pro Gly Pro Pro Gly Pro Arg Gly His Lys
    210                 215                 220

Gly Glu Lys Gly Asp Lys Gly Asp Gln
225                 230

<210> SEQ ID NO 3
<211> LENGTH: 466
<212> TYPE: PRT
<213> ORGANISM: Artificial Sequence
<220> FEATURE:
<223> OTHER INFORMATION: Recombinant human type XVII collagen 170802

<400> SEQUENCE: 3

Gly Ser Pro Gly Pro Lys Gly Asp Met Gly Ser Pro Gly Pro Lys Gly
1               5                   10                  15

Asp Arg Gly Phe Pro Gly Thr Pro Gly Ile Pro Gly Pro Leu Gly His
            20                  25                  30

Pro Gly Pro Gln Gly Pro Lys Gly Gln Lys Gly Ser Val Gly Asp Pro
        35                  40                  45

Gly Met Glu Gly Pro Gly Glu Lys Gly Glu Arg Gly Ala Ala Gly Glu
    50                  55                  60

Pro Gly Pro His Gly Pro Pro Gly Val Pro Gly Ser Val Gly Pro Lys
65                  70                  75                  80

Gly Ser Ser Gly Ser Pro Gly Pro Gln Gly Pro Pro Gly Pro Val Gly
                85                  90                  95

Leu Gln Gly Leu Arg Gly Glu Val Gly Leu Pro Gly Val Lys Gly Asp
            100                 105                 110

Lys Gly Pro Met Gly Pro Pro Gly Pro Lys Gly Asp Gln Gly Glu Lys
        115                 120                 125

Gly Pro Pro Gly Pro Pro Gly Pro Pro Gly Pro Lys Gly Asp Gln Gly
    130                 135                 140

Pro Pro Gly Pro Arg Gly His Gln Gly Glu Gln Gly Leu Pro Gly Phe
145                 150                 155                 160

Ser Gly Pro Pro Gly Pro Pro Gly Pro Gln Gly Pro Lys Gly Asp Lys
                165                 170                 175

Gly Asp Pro Gly Val Pro Gly Ala Leu Gly Ile Pro Gly Pro Pro Gly
            180                 185                 190
```

-continued

```
Gln Lys Gly Glu Met Gly Thr Pro Gly Pro Lys Gly Asp Arg Gly Pro
            195                 200                 205

Ala Gly Pro Pro Gly His Pro Gly Pro Gly Pro Arg Gly His Lys
    210                 215                 220

Gly Glu Lys Gly Asp Lys Gly Asp Gln Gly Ser Pro Gly Pro Lys Gly
225                 230                 235                 240

Asp Met Gly Ser Pro Gly Pro Lys Gly Asp Arg Gly Phe Pro Gly Thr
                245                 250                 255

Pro Gly Ile Pro Gly Pro Leu Gly His Pro Gly Pro Gln Gly Pro Lys
            260                 265                 270

Gly Gln Lys Gly Ser Val Gly Asp Pro Gly Met Glu Gly Pro Gly Glu
        275                 280                 285

Lys Gly Glu Arg Gly Ala Ala Gly Glu Pro Gly Pro His Gly Pro Pro
    290                 295                 300

Gly Val Pro Gly Ser Val Gly Pro Lys Gly Ser Ser Gly Ser Pro Gly
305                 310                 315                 320

Pro Gln Gly Pro Pro Gly Pro Val Gly Leu Gln Gly Leu Arg Gly Glu
                325                 330                 335

Val Gly Leu Pro Gly Val Lys Gly Asp Lys Gly Pro Met Gly Pro Pro
            340                 345                 350

Gly Pro Lys Gly Asp Gln Gly Glu Lys Gly Pro Pro Gly Pro Pro Gly
        355                 360                 365

Pro Pro Gly Pro Lys Gly Asp Gln Gly Pro Pro Gly Pro Arg Gly His
    370                 375                 380

Gln Gly Glu Gln Gly Leu Pro Gly Phe Ser Gly Pro Pro Gly Pro Pro
385                 390                 395                 400

Gly Pro Gln Gly Pro Lys Gly Asp Lys Gly Asp Pro Gly Val Pro Gly
                405                 410                 415

Ala Leu Gly Ile Pro Gly Pro Pro Gly Gln Lys Gly Glu Met Gly Thr
            420                 425                 430

Pro Gly Pro Lys Gly Asp Arg Gly Pro Ala Gly Pro Pro Gly His Pro
        435                 440                 445

Gly Pro Pro Gly Pro Arg Gly His Lys Gly Glu Lys Gly Asp Lys Gly
    450                 455                 460

Asp Gln
465

<210> SEQ ID NO 4
<211> LENGTH: 249
<212> TYPE: PRT
<213> ORGANISM: Artificial Sequence
<220> FEATURE:
<223> OTHER INFORMATION: Optimized amino acid sequence of 170801

<400> SEQUENCE: 4

Tyr Val Trp Ser His Pro Gln Phe Glu Lys Gly Ser Pro Gly Pro Lys
1               5                   10                  15

Gly Asp Met Gly Ser Pro Gly Pro Lys Gly Asp Arg Gly Phe Pro Gly
            20                  25                  30

Thr Pro Gly Ile Pro Gly Pro Leu Gly His Pro Gly Pro Gln Gly Pro
        35                  40                  45

Lys Gly Gln Lys Gly Ser Val Gly Asp Pro Gly Met Glu Gly Pro Gly
    50                  55                  60

Glu Lys Gly Glu Arg Gly Ala Ala Gly Glu Pro Gly Pro His Gly Pro
65                  70                  75                  80
```

```
Pro Gly Val Pro Gly Ser Val Gly Pro Lys Gly Ser Gly Ser Pro
                85                  90                  95

Gly Pro Gln Gly Pro Pro Gly Pro Val Gly Leu Gln Gly Leu Arg Gly
            100                 105                 110

Glu Val Gly Leu Pro Gly Val Lys Gly Asp Lys Gly Pro Met Gly Pro
            115                 120                 125

Pro Gly Pro Lys Gly Asp Gln Gly Glu Lys Gly Pro Pro Gly Pro Pro
            130                 135                 140

Gly Pro Pro Gly Pro Lys Gly Asp Gln Gly Pro Gly Pro Arg Gly
145                 150                 155                 160

His Gln Gly Glu Gln Gly Leu Pro Gly Phe Ser Gly Pro Pro Gly Pro
                165                 170                 175

Pro Gly Pro Gln Gly Pro Lys Gly Asp Lys Gly Asp Pro Gly Val Pro
            180                 185                 190

Gly Ala Leu Gly Ile Pro Gly Pro Gly Gln Lys Gly Glu Met Gly
            195                 200                 205

Thr Pro Gly Pro Lys Gly Asp Arg Gly Pro Ala Gly Pro Pro Gly His
    210                 215                 220

Pro Gly Pro Pro Gly Pro Arg Gly His Lys Gly Glu Lys Gly Asp Lys
225                 230                 235                 240

Gly Asp Gln His His His His His
                245

<210> SEQ ID NO 5
<211> LENGTH: 482
<212> TYPE: PRT
<213> ORGANISM: Artificial Sequence
<220> FEATURE:
<223> OTHER INFORMATION: Optimized amino acid sequence of 170802

<400> SEQUENCE: 5

Tyr Val Trp Ser His Pro Gln Phe Glu Lys Gly Ser Pro Gly Pro Lys
1               5                   10                  15

Gly Asp Met Gly Ser Pro Gly Pro Lys Gly Asp Arg Gly Phe Pro Gly
                20                  25                  30

Thr Pro Gly Ile Pro Gly Pro Leu Gly His Pro Gly Pro Gln Gly Pro
            35                  40                  45

Lys Gly Gln Lys Gly Ser Val Gly Asp Pro Gly Met Glu Gly Pro Gly
    50                  55                  60

Glu Lys Gly Glu Arg Gly Ala Ala Gly Glu Pro Gly Pro His Gly Pro
65              70                  75                  80

Pro Gly Val Pro Gly Ser Val Gly Pro Lys Gly Ser Gly Ser Pro
                85                  90                  95

Gly Pro Gln Gly Pro Pro Gly Pro Val Gly Leu Gln Gly Leu Arg Gly
            100                 105                 110

Glu Val Gly Leu Pro Gly Val Lys Gly Asp Lys Gly Pro Met Gly Pro
            115                 120                 125

Pro Gly Pro Lys Gly Asp Gln Gly Glu Lys Gly Pro Pro Gly Pro Pro
            130                 135                 140

Gly Pro Pro Gly Pro Lys Gly Asp Gln Gly Pro Gly Pro Arg Gly
145                 150                 155                 160

His Gln Gly Glu Gln Gly Leu Pro Gly Phe Ser Gly Pro Pro Gly Pro
                165                 170                 175

Pro Gly Pro Gln Gly Pro Lys Gly Asp Lys Gly Asp Pro Gly Val Pro
            180                 185                 190
```

Gly Ala Leu Gly Ile Pro Gly Pro Gly Gln Lys Gly Glu Met Gly
            195                 200                 205

Thr Pro Gly Pro Lys Gly Asp Arg Gly Pro Ala Gly Pro Gly His
    210                 215                 220

Pro Gly Pro Gly Pro Arg Gly His Lys Gly Glu Lys Gly Asp Lys
225                 230                 235                 240

Gly Asp Gln Gly Ser Pro Gly Pro Lys Gly Asp Met Gly Ser Pro Gly
                245                 250                 255

Pro Lys Gly Asp Arg Gly Phe Pro Gly Thr Pro Gly Ile Pro Gly Pro
                260                 265                 270

Leu Gly His Pro Gly Pro Gln Gly Pro Lys Gly Gln Lys Gly Ser Val
            275                 280                 285

Gly Asp Pro Gly Met Glu Gly Pro Gly Glu Lys Gly Glu Arg Gly Ala
    290                 295                 300

Ala Gly Glu Pro Gly Pro His Gly Pro Pro Gly Val Pro Gly Ser Val
305                 310                 315                 320

Gly Pro Lys Gly Ser Ser Gly Ser Pro Gly Pro Gln Gly Pro Pro Gly
                325                 330                 335

Pro Val Gly Leu Gln Gly Leu Arg Gly Glu Val Gly Leu Pro Gly Val
                340                 345                 350

Lys Gly Asp Lys Gly Pro Met Gly Pro Pro Gly Pro Lys Gly Asp Gln
            355                 360                 365

Gly Glu Lys Gly Pro Pro Gly Pro Pro Gly Pro Pro Gly Pro Lys Gly
    370                 375                 380

Asp Gln Gly Pro Pro Gly Pro Arg Gly His Gln Gly Glu Gln Gly Leu
385                 390                 395                 400

Pro Gly Phe Ser Gly Pro Pro Gly Pro Pro Gly Pro Gln Gly Pro Lys
                405                 410                 415

Gly Asp Lys Gly Asp Pro Gly Val Pro Gly Ala Leu Gly Ile Pro Gly
                420                 425                 430

Pro Pro Gly Gln Lys Gly Glu Met Gly Thr Pro Gly Pro Lys Gly Asp
            435                 440                 445

Arg Gly Pro Ala Gly Pro Pro Gly His Pro Gly Pro Pro Gly Pro Arg
    450                 455                 460

Gly His Lys Gly Glu Lys Gly Asp Lys Gly Asp Gln His His His His
465                 470                 475                 480

His His

<210> SEQ ID NO 6
<211> LENGTH: 699
<212> TYPE: DNA
<213> ORGANISM: Artificial Sequence
<220> FEATURE:
<223> OTHER INFORMATION: DNA sequence encoding 170801

<400> SEQUENCE: 6
ggttctcctg gtccaaaagg tgacatgggt tctccaggtc ctaaaggtga cagaggtttt      60
cctggtactc caggtattcc tggtccattg ggtcatccag gtcctcaagg tccaaaaggt     120
caaaagggtt ctgttggtga ccctggtatg gaaggtccag gtgaaaaggg tgaaagaggt     180
gctgctggtg aacctggtcc acacggtcca cctggtgttc caggttctgt tggtcctaag     240
ggttcttctg gttctcctgg tccacaaggt cctcctggtc cagttggttt gcaaggtttg     300
agaggtgaag ttggtttgcc aggtgttaag ggtgacaagg gtccaatggg tcctccaggt     360
ccaaaaggtg accaaggtga aaagggtcca cctggtcctc ctggtccacc tggtccaaag     420

```
ggtgaccaag gtcctccagg tcctagaggt catcaaggtg aacaaggttt gcctggtttt    480
tctggtccac caggtcctcc aggtccacaa ggtcctaaag gtgacaaagg tgacccaggt    540
gttcctggtg ctttgggtat tccaggtcca cctggtcaaa aggtgaaatg ggtactcca     600 ggtcctaagg gtgacagagg tccagctggt ccacctggtc atcctggtcc accaggtcca   660
agaggtcata aggtgaaaa aggtgacaag ggtgaccaa                            699
```

<210> SEQ ID NO 7
<211> LENGTH: 1398
<212> TYPE: DNA
<213> ORGANISM: Artificial Sequence
<220> FEATURE:
<223> OTHER INFORMATION: DNA sequence encoding 170802

<400> SEQUENCE: 7

```
ggttctccag gtcctaaagg tgacatgggt tctccaggtc ctaagggtga cagaggtttt    60
ccaggtactc caggtattcc aggtcctttg ggtcatccag gtcctcaagg tcctaaaggt   120
caaaaaggtt ctgttggtga ccctggtatg aaggtcctg gtgaaaaagg tgaagaggt     180 gctgctggta aacctggtcc acacggtcct ccaggtgttc ctggttctgt tggtccaaaa   240
ggttcttctg gttctcctgg tccacaaggt cctccaggtc ctgttggttt gcaaggtttg   300
agaggtgaag ttggtttgcc agtgttaaa ggtgacaaag gtccaatggg tcctccaggt   360
ccaaagggtg accaaggtga aaaaggtcca cctggtcctc ctggtccacc aggtccaaaa   420
ggtgaccaag gtccacctgg tccaagaggt caccaaggtg aacaaggttt gcctggtttt   480
tctggtcctc caggtcctcc tggtcctcaa ggtccaaagg gtgacaaggg tgaccctggt   540
gttccaggtg ctttgggtat tcctggtcct caggtcaaa agggtgagat gggtactcct   600
ggtcctaagg gtgacagagg tccagctggt cctcctggtc acccaggtcc tcctggtcct   660
agaggtcata aggtgaaaa aggtgacaag ggtgaccaag gttctccagg tccaaagggt   720
gacatgggtt ctcctggtcc aaaaggtgac agaggtttcc ctggtactcc aggtattcct   780
ggtccattgg gtcacccagg tccacaaggt ccaaaaggtc aaaaaggttc tgttggtgac   840
ccaggtatgg aaggtccagg tgaaaagggt gaaagaggt ctgctggtga accaggtcct   900
catggtccac caggtgttcc aggttctgtt ggtccaaagg gttcttctgg ttctccaggt   960
ccacaaggtc ctccaggtcc agttggtttg caagggtttga gaggtgaagt tggtttgcct  1020
ggtgttaagg gtgacaaagg tcctatgggt cctcctggtc ctaaaggtga ccaaggtgaa  1080
aagggtccac caggtcctcc aggtccacct ggtccaaaag gtgaccaagg tccaccaggt  1140
cctagaggtc atcaaggtga acaaggtttg ccaggttttt ctggtccacc aggtccacca  1200
ggtcctcaag gtcctaaggg tgacaaaggt gacccaggtt tcctggtgc tttgggtatt  1260 cctggtccac ctggtcaaaa gggtgaaatg ggtactcctg gtcctaaagg tgacagaggt  1320
cctgctggtc cacctggtca tccaggtcca cctggtccaa gaggtcacaa aggtgaaaag  1380
ggtgacaagg gtgaccaa                                                 1398
```

<210> SEQ ID NO 8
<211> LENGTH: 758
<212> TYPE: DNA
<213> ORGANISM: Artificial Sequence
<220> FEATURE:
<223> OTHER INFORMATION: Synthetic DNA sequence

<400> SEQUENCE: 8

```
tacgtatggt ctcatccaca attcgagaag ggttctcctg gtccaaaagg tgacatgggt      60
tctccaggtc ctaaaggtga cagaggtttt cctggtactc caggtattcc tggtccattg     120
ggtcatccag gtcctcaagg tccaaaaggt caaaagggtt ctgttggtga ccctggtatg     180
gaaggtccag gtgaaaaggg tgaaagaggt gctgctggtg aacctggtcc acacggtcca     240
cctggtgttc caggttctgt tggtcctaag ggttcttctg gttctcctgg tccacaaggt     300
cctcctggtc cagttggttt gcaaggtttg agaggtgaag ttggttttgcc aggtgttaag     360 ggtgacaagg gtccaatggg tcctccaggt ccaaaaggtg accaaggtga aaagggtcca     420
cctggtcctc ctggtccacc tggtccaaag ggtgaccaag gtcctccagg tcctagaggt     480
catcaaggtg aacaaggttt gcctggtttt tctggtccac aggtcctcc aggtccacaa      540 ggtcctaaag gtgacaaagg tgacccaggt gttcctggtg ctttgggtat tccaggtcca     600
cctggtcaaa aggtgaaat gggtactcca ggtcctaagg gtgacagagg tccagctggt      660
ccacctggtc atcctggtcc accaggtcca agaggtcata agggtgaaaa aggtgacaag     720
ggtgaccaac accatcatca ccatcattaa gcggccgc                             758
```

<210> SEQ ID NO 9
<211> LENGTH: 1457
<212> TYPE: DNA
<213> ORGANISM: Artificial Sequence
<220> FEATURE:
<223> OTHER INFORMATION: Synthetic DNA sequence

<400> SEQUENCE: 9

```
tacgtatggt ctcatcctca atttgaaaag ggttctccag gtcctaaagg tgacatgggt      60
tctccaggtc ctaagggtga cagaggtttt ccaggtactc caggtattcc aggtcctttg     120
ggtcatccag gtcctcaagg tcctaaaggt caaaaaggtt ctgttggtga ccctggtatg     180
gaaggtcctg gtgaaaaagg tgaaagaggt gctgctggtg aacctggtcc acacggtcct     240
ccaggtgttc ctggttctgt tggtccaaaa ggttcttctg gttctcctgg tccacaaggt     300
cctccaggtc ctgttggttt gcaaggtttg agaggtgaag ttggttttgcc aggtgttaaa     360 ggtgacaaag gtccaatggg tcctccaggt ccaaagggtg accaaggtga aaaaggtcca     420
cctggtcctc ctggtccacc aggtccaaaa ggtgaccaag gtccacctgg tccaagaggt     480
caccaaggtg aacaaggttt gcctggtttt tctggtcctc aggtcctcc tggtcctcaa      540 ggtccaaagg gtgacaaggg tgaccctggt gttccaggtg ctttgggtat tcctggtcct     600
ccaggtcaaa agggtgagat gggtactcct ggtcctaagg gtgacagagg tccagctggt     660
cctcctggtc acccaggtcc tcctggtcct agaggtcata agggtgaaaa aggtgacaag     720
ggtgaccaag gttctccagg tccaaagggt gacatgggtt ctcctggtcc aaaaggtgac     780
agaggtttcc ctggtactcc aggtattcct ggtccattgg gtcacccagg tccacaaggt     840
ccaaaaggtc aaaaggttc tgttggtgac ccaggtatgg aaggtccagg tgaaaagggt      900
gaaagaggtg ctgctggtga accaggtcct catggtccac aggtgttcc aggttctgtt      960 ggtccaaagg gttcttctgg ttctccaggt ccacaaggtc ctccaggtcc agttggtttg    1020
caaggtttga gaggtgaagt tggttttgcct ggtgttaagg gtgacaaagg tcctatgggt    1080
cctcctggtc ctaaaggtga ccaaggtgaa aagggtccac caggtcctcc aggtccacct    1140
ggtccaaaag gtgaccaagg tccaccaggt cctagaggtc atcaaggtga acaaggtttg    1200
ccaggttttt ctggtccacc aggtccacca ggtcctcaag gtcctaaggg tgacaaaggt    1260
gacccaggtg ttcctggtgc ctttgggtatt cctggtccac ctggtcaaaa gggtgaaatg    1320
```

```
ggtactcctg gtcctaaagg tgacagaggt cctgctggtc cacctggtca tccaggtcca    1380
cctggtccaa gaggtcacaa aggtgaaaag ggtgacaagg gtgaccaaca ccatcaccat    1440
catcattaag cggccgc                                                   1457
```

<210> SEQ ID NO 10
<211> LENGTH: 4550
<212> TYPE: DNA
<213> ORGANISM: Artificial Sequence
<220> FEATURE:
<223> OTHER INFORMATION: Synthetic DNA sequence

<400> SEQUENCE: 10

```
gaattctgga gtcatcctca attcgaaaaa atggatgtca ctaaaaagaa caagagagac      60
ggaactgagg tcactgagag aatcgttacc gaaactgtca ccacaagact tacttcatta    120
cctccaaagg gtggaacttc taatggttac gcaaagacag catcattagg aggtggttca    180
agacttgaga acaatccct tactcatggt tcaagtggat acataaattc aactggttca    240
acaagaggac atgcaagtac ttcttcttat agaagagcac atagtccagc atcaactttg    300
cccaactctc ctggttcaac atttgagaga aaaactcatg taaccagaca tgcctatgag    360
ggttctagtt ctggtaattc atctccagaa tacctagaa aagagtttgc atcatcctca    420
actagaggta gatcacagac tagagaatct gaaatcagag tcagattaca atcagcatct    480
ccttcaacta gatggactga gttagacgac gtgaaaagat tattaaaggg atcaagaagt    540
gcaagtgttt cccctacaag aaattcttcc aacacccttc ccattcctaa gaaaggaacc    600
gttgaaacta aaatcgttac agcatcatct cagtctgtat ccggaaccta cgacgctacc    660
attctggacg ccaacttacc ttctcatgtc tggtcttcaa ctttacccgc aggttcctca    720
atgggaactt accacaataa catgactact caatcaagtt ctcttctgaa taccaatgca    780
tactcagccg gttccgtttt tggagtccct aacaatatgg cctcttgctc cccaactctt    840
catccaggtc tttcaacctc atcaagtgta tttggtatgc agaacaactt agccccttcc    900
ttgacaaccc tgtctcatgg tactactacc actagtacag catatggagt caagaagaac    960
atgccacagt cacctgctgc cgttaacact ggagtttcaa catctgctgc ctgcactaca   1020
tctgttcaat cagatgatct tctgcataag gactgcaagt tttaattttt agagaaagac   1080
aatacccctg ccaaaaagga aatggagtta cttataatga ccaaagattc tggtaaagta   1140
ttcactgctt ctcccgctag tatcgccgca acttcattct ctgaagatac tttaaagaag   1200
gaaaaacaag ccgcatacaa cgcagactca ggtttaaaag cagaagcaaa cggtgacctt   1260
aaaacagtgt caactaaggg aaagactaca accgcagaca tccattcata tggttcttca   1320 ggtgaggag atctggagg aggtggtgga gtggaggtg ctggaggag tccatggggt       1380 cctgcacctg catggtgccc ttgcggttct tgctgcagtt ggtggaagtg gcttctgggt   1440
ttattattaa cttggctgct tttactgggt cttttattcg gtcttatcgc attagcagaa   1500
gaggtcagaa aacttaaggc cagagttgat gagttagaga gaatcagaag atcaatcctt   1560
ccctatggag actccatgga cagaatcgaa aaggatagac ttcagggtat ggcccctgca   1620
gcaggagctg atctggataa aatcggactt cattcagatt ctcaagagga attatggatg   1680
tttgttagaa agaaacttat gatggagcag gagaacggta acctgagagg ttctcctggt   1740
ccaaaaggag atatgggttc acccggtccc aaaggagata gaggattccc tggtactcca   1800
ggtatccccg gtcccctggg tcaccctgga cctcaaggtc ctaaaggtca aagggttct   1860
```

```
gtaggagatc caggtatgga gggtcccatg ggtcagagag gtagagaagg tcccatggga   1920
ccaagaggtg aagctggacc tcccggaagt ggtgaaaaag gagaaagagg agcagcagga   1980
gaacctggac cccatggacc tccaggagtt cctggatcag tcggacccaa aggttcatcc   2040
ggttctcctg gacctcaagg tccaccagga cccgtcggat tgcaaggatt gagaggagaa   2100
gttggacttc ccggagttaa gggtgacaag ggtcctatgg gtcctcctgg tccaaaggga   2160
gatcagggtc aaaagggtcc tagaggtctg actggtgaac caggaatgag aggacttccc   2220
ggtgccgtgg gtgaacccgg tgcaaaagga gcaatgggtc ctgccggtcc tgatggacac   2280
cagggaccca gaggagagca gggattaaca ggaatgcctg gtatcagagg tcccccaggt   2340
ccctcaggag acccaggaaa gccaggactt actggtcccc agggtcctca aggtctgcct   2400
ggaactcccg gaagacccgg aatcaaaggt gaaccaggag ccccaggaaa aatcgttact   2460
agtgaaggat cttcaatgct gactgtgcca ggtccacctg gtcctcctgg agctatgggt   2520
cctcccggtc ccctggagc acccggtcct gcaggtcctg ccggattacc tggacatcag   2580
gaagtcttaa acctgcaagg tccaccaggt cctcctggtc aagaggacc ccctggtcct   2640 tcaatccctg gtccacctgg acctagaggt ccacccggag agggacttcc cggaccacca   2700
ggacctcctg gatcatttct gtctaattct gagacatttc tttcaggacc tcctggtcct   2760
cccggaccac ctggaccaaa aggagatcag ggaccacctg gtcccagagg acatcaagga   2820
gagcagggtc ttcaggtttt ctctacttct ggatcatcat catttggtct taatcttcaa   2880
ggtcctcctg gacccccagg accacaggga cccaagggtg acaagggaga ccctggagtc   2940
ccaggtgcac tgggaatccc ttcaggtcct tcagaaggtg gttcatcttc aaccatgtat   3000
gtgtctggac ccccaggacc tcccggacct ccaggtcctc ctggttcaat ctcttcttct   3060
ggtcaagaaa ttcagcagta tatttctgag tacatgcaat ctgactctat tagaagttat   3120
ttgtctggtg tgcagggtcc accaggtcct ccaggtccc ctggaccagt cactactatc   3180
actggagaga catttgatta tagtgaatta gcatcacacg tcgtttctta tctgagaact   3240
tcaggttatg gtgtttcatt attttcctcc tcaatctctt cagaagacat cttagccgta   3300
ctgcagagag atgatgtaag acagtacctt agacaatact tgatgggtcc aagaggacca   3360
ccaggtccac ccggtgcatc aggagacgga tcattattat ctttggatta cgctgaatta   3420
tcatcaagaa tccttagtta catgtcctct tctggtatct ccataggtct gcccggtcct   3480
cctggtcctc ccggacttcc tggtacttct tacgaagagc ttctgtcact tttaagagga   3540
tctgagttta gaggtatagt tggtcccca ggacctccag gtcctccagg tatcccaggt   3600
aacgtgtggt catctatctc agttgaggat cttcatctt atcttcacac cgccggattg   3660
tcctttatac ctggtcctcc aggacccct ggacctcctg acccagagg tcctccagga   3720 gtatccggtg ctttagcaac ttatgcagca gaaaactccg attctttag atcagaattg   3780 atctcctacc ttacttctcc tgatgttaga tcattcatcg tcggacctcc aggaccacct   3840
ggacctcaag gacctcctgg agattcaaga ttactgagta cagatgcatc acattcaaga   3900
ggttcaagtt cttcttctca ctcctcttct gttagaagag gatcatcata ttcatcaagt   3960
atgtcaactg gtggaggagg agctggttca ttgggtgccg gaggtgcatt tggtgaggcc   4020
gctggtgaca gaggacctta tggtactgac attggacctg gtggaggtta tggtgcagca   4080
gcagaaggtg gaatgtatgc tggtaatgga ggtttactgg gagccgactt tgccggagac   4140
ctggactaca acgagttagc tgttagagtg tcagagtcaa tgcagagaca aggattatta   4200
cagggtatgg cttatacagt tcagggaccc ccaggtcagc caggtcctca aggaccccct   4260
```

```
ggtatttcaa aagtcttctc cgcttattct aacgttactg cagacctgat ggatttcttc    4320
cagacttacg gtgccatcca aggtcctcca ggacagaagg gtgaaatggg aactcccggt    4380
cccaagggtg acagaggtcc tgcaggacct cctggtcacc ctggaccacc tggacctaga    4440
ggacacaaag gtgagaaggg tgacaaggga gaccaggttt acgcaggaag aagaagaaga    4500
agaagtattg ccgtcaagcc tcaccatcac catcatcact aagcggccgc               4550
```

RECOMBINANT HUMAN TYPE XVII COLLAGEN, AND PREPARATION METHOD AND USE THEREOF

CROSS REFERENCE TO THE RELATED APPLICATIONS

This application is the national phase entry of International Application No. PCT/CN2022/071968, filed on Jan. 14, 2022, which is based upon and claims priority to Chinese Patent Application No. 202110520499.9, filed on May 13, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBNJIP071-Sequence-listing.txt, created on 08/10/2022, and is 38,385 bytes in size.

TECHNICAL FIELD

The present disclosure relates to a recombinant human type XVII collagen, and a preparation method and use thereof, and belongs to the technical field of genetic engineering.

BACKGROUND

As an important native biological protein, collagen can be widely used in many fields such as chemical industry, medicine, food, and cosmetics, and is especially suitable for the manufacture of various biological devices. Collagen is the most ideal biological material source and has promising application prospects. Collagen sold currently on the market is mainly a collagen extract obtained by treating an animal tissue through acid, alkali, and enzymatic hydrolysis. During the processing of such an extract, a native structure of collagen is basically destroyed and is severely degraded, making its biological activity lost; extracted collagen peptides have different lengths, heterogeneous properties, and unstable qualities, and may be infected by a virus; and an amino acid sequence of animal-derived collagen is quite different from an amino acid sequence of human-derived collagen, which can lead to immune rejection and allergic symptoms.

Human type XVII collagen is a transmembrane non-fibroblast collagen, which is a homogeneous trimer composed of three identical α1 (XVII) chains and is divided into three major domains: intracellular, transmembrane, and extracellular domains. Human type XVII collagen is a component of hemidesmosomes in cells, plays an important role in an interaction between epithelial cells and a basement membrane, can regulate the adhesion, separation, development, and differentiation of epithelial cells, and is important for the differentiation and regeneration of keratinocytes. Because a content of human type XVII collagen in the human body is very low and a content of type XVII collagen in an animal is also extremely low, type XVII collagen is very difficult to extract and cannot be mass-produced. Moreover, animal-derived collagen products inevitably have immunogenicity and potential biological safety hazards such as viruses and epidemics, and thus are not widely used. Limited by legal and ethical constraints, human type XVII collagen can only be used in scientific research, and thus there are currently no commercial human-derived or animal-derived type XVII collagen products on the market, which further limits the research and application of human type XVII collagen. A main way for solving such problems now is to produce collagen through a biotechnology such as genetic engineering.

Existing recombinant proteins are mainly produced by the following four expression systems: prokaryotic (*Escherichia coli* (*E. coli*)) expression system, *Pichia pastoris* (*P. pastoris*) expression system, mammalian cell expression system, and insect cell (baculovirus) expression system. There are few studies on the expression of human type XVII collagen in mammalian cells, which are all in an experimental investigation stage. The prokaryotic expression system (such as *E. coli* and pGEX expression vector) was first used in the production of a fusion protein of a non-helical region NC16 sequence, and there is no report on the successful expression of human type XVII collagen by the remaining expression systems, especially the *P. pastoris* expression system.

The expression in mammalian cells involves a high expression cost and a low yield, and thus mammalian cells are mostly used for the expression and production of high-value pharmaceutical proteins. When human type XVII collagen is expressed in mammalian cells either by transient transfection or stable transfection, an expression level of the protein is extremely low, and a medium used is expensive such that only the need of trace consumption in scientific research can be met. The insect cell (baculovirus) expression system not only has a high cost and a low yield, but also shows a huge difference from human cells in post-translation. Therefore, these two methods are generally not used for the mass production of collagen. Collagen obtained by the prokaryotic expression system (*E. coli* expression system) has no post-translational modification. The prokaryotic expression with the prospect of large-scale amplification can only be achieved intracellularly, such that bacterial lysis is required and a large amount of impurity protein will be mixed with the target protein, which presents extremely high requirements on a purification process. Moreover, the prokaryotic expression system naturally carries the components of a bacterial cell wall such as endotoxin and peptidoglycan, which require complicated purification processes to remove.

Collagen products from the above expression systems have sequence singleness and low biological activity, for example, the sequence selection is relatively single, and collagen peptides are all expressed independently, but an extracellular domain of the human type XVII collagen includes nearly 1,000 amino acids (divided into 15 triple-helix regions and 15 non-triple-helix regions), which results in sequence abundance. Among the biological activities of collagen, the cell adhesion activity is merely the most basic one, and the remaining biological activities are not involved. Moreover, whether the mammalian cell expression or the *E. coli* expression is only used in the small-volume laboratory-level cultivation and production, and does not involve no large-scale production. However, the application of recombinant collagen is enabled on the premise of large-scale, high-density, and high-expression fermentation production and purification, and generally, after the verification of a 500 L pilot fermentation experiment, it is possible to achieve industrial-scale and large-scale production.

There are some difficulties in the expression of human type XVII collagen. The human type XVII collagen is a transmembrane collagen, which has an intracellular region, a transmembrane region, and an extracellular region. Generally, when expressed in eukaryotic cells, transmembrane proteins are mostly not secreted extracellularly, but are fixed on a cell membrane. In addition, with a very long amino acid sequence (1,497 amino acids) and a large protein molecular weight (180 kDa), the human type XVII collagen is theoretically difficult to be effectively secreted extracellularly and easy to be degraded. Therefore, the selection of relevant sequences is required for successful expression. At present, little research on the amino acid sequence, structure, and function of the human type XVII collagen is known. Therefore, how to select an amino acid sequence that can achieve abundant biological functions on the premise of retaining the advantages of the *P. pastoris* expression system (especially the secretory expression) is a prominent difficulty, which is also a difficulty for the expression of human type XVII collagen in other expression systems (including *E. coli*).

SUMMARY

The present disclosure is intended to overcome some technical problems in the prior art that how to achieve the optimal selection of a recombinant human type XVII collagen sequence (non-singleness) and the efficient secretory expression of the recombinant human type XVII collagen sequence in *P. pastoris*, the existing recombinant human type XVII collagen has only cell adhesion activity, and the existing recombinant human type XVII collagen cannot be produced on a large scale.

In view of this, the present disclosure provides a collagen, a polynucleotide encoding the collagen, a recombinant vector that carries the polynucleotide encoding the collagen, an engineered bacterium, a preparation method of the collagen, a composition including the collagen, and use of the collagen. In the present disclosure, it is confirmed that the collagen is a human type XVII collagen that can undergo efficient secretory and soluble expression in eukaryotic host cells such as *P. pastoris*, exhibits more excellent cell adhesion activity, cell migration-promoting activity, tissue regeneration-promoting activity, and hair follicle repair and regeneration-promoting activity than commercial native human collagen, and can be used industrially.

The present disclosure provides a collagen that has cell adhesion activity, cell migration-promoting activity, tissue regeneration-promoting activity, and hair follicle repair and regeneration-promoting activity.

The collagen consists of an amino acid sequence shown in $(A)_n$ or includes the amino acid sequence shown in $(A)_n$ where A is an amino acid sequence set forth in SEQ ID NO: 2, an amino acid sequence undergoing a modification such as amino acid replacement, insertion, substitution, addition, or deletion to a predetermined extent based on SEQ ID NO: 2, or an amino acid sequence that has more than 80% homology with SEQ ID NO: 2; n is an integer greater than or equal to 1; and A represents a basic unit, and when there are two or more basic units, the two or more basic units are identical or different and are directly connected in tandem through a peptide bond.

Further, according to an embodiment of the present disclosure, the collagen consists of an amino acid sequence shown in $(A)_n$ or includes the amino acid sequence shown in $(A)_n$ where A is an amino acid sequence set forth in SEQ ID NO: 2; n is an integer greater than or equal to 1; and A represents a basic unit, and when there are two or more basic units, the two or more basic units are identical and are directly connected in tandem through a peptide bond.

Further, according to an embodiment of the present disclosure, the collagen consists of an amino acid sequence shown in $(A)_n$ where when n is 1, the collagen has an amino acid sequence set forth in SEQ ID NO: 2, which is denoted as 170801 in the present disclosure; and when n is 2, the collagen has an amino acid sequence set forth in SEQ ID NO: 3, which is denoted as 170802 in the present disclosure.

Further, according to the present disclosure, the collagen of the present disclosure consists of an amino acid sequence shown in $(A)_n$ or includes the amino acid sequence shown in $(A)_n$, where A is an amino acid sequence undergoing a modification such as amino acid insertion, substitution, addition, or deletion to a predetermined extent based on SEQ ID NO: 2 or an amino acid sequence that has more than 80% homology with SEQ ID NO: 2; n is an integer greater than or equal to 1; and A represents a basic unit, and when there are two or more basic units, the two or more basic units are identical or different and are directly connected in tandem through a peptide bond.

The present disclosure also provides a polynucleotide encoding the collagen, specifically a polynucleotide sequence encoding the collagen represented by $(A)_n$. Preferably, when *P. pastoris* is used as a host cell, the polynucleotide includes a nucleotide sequence selected from the group consisting of SEQ ID NO: 6 and SEQ ID NO: 7 or consists of a nucleotide sequence selected from the group consisting of SEQ ID NO: 6 and SEQ ID NO: 7.

According to an embodiment of the present disclosure, the A is SEQ ID NO: 2, and when n is 1, the polynucleotide is a nucleotide sequence set forth in SEQ ID NO: 6. According to an embodiment of the present disclosure, the A is SEQ ID NO: 2, and when n is 2, the polynucleotide encoding the $(A)_n$ is a nucleotide sequence set forth in SEQ ID NO: 7.

The collagen of the present disclosure has a combined sequence obtained after optimization and screening of multiple helix region sequences of human type XVII collagen such as the 15th helix region, the carboxyl terminus region, and the middle region, which is 100% identical to a corresponding part of an amino acid sequence of human type XVII collagen. The recombinant collagen of the present disclosure can undergo efficient secretory and soluble expression in eukaryotic host cells such as *P. pastoris*, and exhibits more excellent cell adhesion activity, cell migration-promoting activity, tissue regeneration-promoting activity, and hair follicle repair and regeneration-promoting activity than commercial native human collagen. Such a combined sequence enables the integration of functions of the respective region sequences, such that the respective region sequences are not expressed separately but expressed as a whole, which avoids the sequence singleness of the recombinant collagen.

The present disclosure also provides a recombinant expression vector that carries the polynucleotide encoding the collagen.

According to an embodiment of the present disclosure, during a construction process of the recombinant expression vector of the present disclosure, the polynucleotide encoding the collagen represented by $(A)_n$ is modified first, by adding a DNA sequence encoding a Strep-Tag II to an amino terminus of the amino acid sequence of the collagen, and adding a DNA sequence encoding a hexahistidine Tag to a carboxyl terminus of the amino acid sequence of the collagen, such that the collagen contains bispecific affinity purification tags, which enables the purification by affinity chromatography and the immunological antibody detection based on the two tag sequences, and then the labeled sequence is ligated into an expression vector pPIC9K to construct the recombinant expression vector (represented by pPIC9K-170801 and pPIC9K-170802 in the examples).

The present disclosure also provides an engineered bacterium constructed from the recombinant expression vector, and a host cell for the engineered bacterium is preferably *P. pastoris*. The engineered bacterium was deposited in the China General Microbiological Culture Collection Center (CGMCC) located at No. 1, West Beichen Road, Chaoyang District, Beijing, China on Sep. 9, 2020, with an accession number of CGMCC NO. 20626 or CGMCC NO. 20627 and a taxonomic name of *Pichia pastoris*.

It should be noted that the host cell can be a eukaryotic cell, such as a fungal cell, a yeast cell, and a plant cell; a prokaryotic cell, such as Enterobacteriaceae, such as *E. coli*; or an animal cell, such as a mammalian cell such as a CHO cell line and an HEK293 cell line or an insect cell. It should be understood that those skilled in the art can use another expression host as an expression host instead of the above *P. pastoris* to express a collagen with the same amino acid sequence.

The present disclosure also provides a preparation method of the collagen, including the following steps:
(1) Cultivation and Screening of Engineered Bacteria
   constructing and screening engineered bacteria, and conducting inducible expression with a Buffered Glycerol-complex Medium (BMGY medium) to obtain an engineered bacterium with high expression, where the engineered bacterium with high expression screened out is *P. pastoris* with an accession number of CGMCC No. 20626 or CGMCC No. 20627; and
(2) Large-Scale High-Density Fermentation, Cultivation, and Protein Purification
   conducting linked fed-batch fermentation in a 50 L to 500 L fermentation tank to obtain a fermentation supernatant, and purifying the fermentation supernatant to obtain a high-purity collagen.

According to an embodiment of the present disclosure, the recombinant expression vector is linearized with Sac I and then electrotransformed into *P. pastoris* competent cells to construct engineered bacteria. The engineered bacteria are transferred to an MD plate for primary screening and then screened on YPD plates with different G418 concentrations, and then colonies are picked and inoculated into a BMGY medium and then subjected to inducible expression in a Buffered Glycerol-complex Medium (BMMY medium), and multiple strains are picked, and the engineered bacterium with high expression is selected for subsequent experiments. In the present disclosure, the expressed protein is preliminarily identified by sodium dodecyl sulfate-polyacrylamide gel electrophoresis (SDS-PAGE) and Western Blot to determine the efficient secretory expression ability, and the results show that the recombinant human type XVII collagen of the present disclosure can undergo efficient secretory expression, while the full-length human type XVII collagen is mainly concentrated in cells and cannot be effectively secreted extracellularly and a target band obtained by electrophoresis is subjected to nanoscale high-performance liquid chromatography coupled to tandem mass spectrometry (Nano-HPLC-MS/MS), and the results show that a peptide in the target band is derived from the optimally selected region in the human type XVII collagen sequence, and the recombinant human type XVII collagens 170801 and 170802 of the present disclosure are successfully expressed.

When a 50 L to 500 L fermentation tank is used to conduct inducible expression for 48 h, yields of the collagens (quantification by UV spectrometry) of the present disclosure can reach 12 g/L and 11 g/L, respectively.

In the present disclosure, a molecular weight is determined by matrix-assisted laser desorption ionization time-of-flight mass spectrometry (MALDI-TOF MS), and the determination results show that a molecular weight of collagen 170801 is 23811.6797 Da (theoretical value: 23800 Da), and a molecular weight of collagen 170802 is 45689.5781 Da (theoretical value: 45400 Da), and while there are post-translational modification and systematic errors in molecular weight determination after expression in *P. pastoris*, the actually expressed collagen has a molecular weight consistent with the theoretical value. The collagen is subjected to infrared (IR) spectroscopy, and it can be seen that wave numbers of amide A, amide B, amide I, amide II, and amide III of the collagen are all in line with the structural characteristics of the recombinant collagen. A purified lyophilized collagen sponge is subjected to scanning electron microscopy, and it can be seen that the collagen sponge has a lamellar structure and has the potential to be used in the field of biomedical materials.

According to an embodiment of the present disclosure, the biological activity of the obtained collagen is detected by in vitro cell experiments, and it is verified that the collagen has cell adhesion activity and cell migration-promoting activity. Animal experiments are conducted for the biological activity of the obtained collagen, and a rabbit ear scar model experiment shows that the collagen can effectively promote rabbit ear scar healing and tissue regeneration, and particularly exhibits extremely excellent activity to promote hair follicle repair and regeneration.

In view of this, the present disclosure also provides use of the collagen described above in the promotion of tissue regeneration or hair follicle repair.

The present disclosure also provides a composition including the collagen described above or a collagen prepared by the preparation method described above.

The present disclosure also provides an article including the collagen described above or a collagen prepared by the preparation method described above or the composition described above. The article includes, but is not limited to, a drug, a pharmaceutical composition, a medical device, a biological material, a tissue-engineered product, a cosmetic, and a health product.

The present disclosure also provides use of the collagen, the polynucleotide, the recombinant expression vector, the engineered bacterium, or the composition in the manufacture of a product, including but not limited to, a drug, a pharmaceutical composition, a medical device, a biological material, a tissue-engineered product, a cosmetic, and a health product.

The present disclosure also provides use of the collagen, the polynucleotide, the recombinant expression vector, the engineered bacterium, or the composition in the manufacture of a product for promoting scar healing, tissue repair, or hair follicle repair. According to an embodiment of the present disclosure, the product is an external preparation, preferably an external preparation for a topical application, and more preferably a gel.

The present disclosure has the following beneficial effects.
(1) The present disclosure adopts the *P. pastoris* expression system. *P. pastoris* is a eukaryotic microorganism with all organelles of a eukaryote, which can perform a post-translational modification (especially a glycosylation modification) on a translated protein to effectively support the realization of biological functions of the protein. The expression system established using *P. pastoris* has large-scale industrial production advantages of the microorganism expression system such as high-density fermentation production, extremely-low cultivation cost, short cycle, and high expression, the expressed protein can be secreted extracellularly in the expression system, which can completely avoid impurity proteins caused by bacterial lysis, and the cell wall of *P. pastoris* does not contain endotoxin and peptidoglycan.

(2) An amino acid sequence of the recombinant human type XVII collagen in the present disclosure is a combination of sequences screened and optimized, and has 100% homology with the corresponding part of the amino acid sequence of the native collagen. Therefore, the recombinant human type XVII collagen has no immunogenicity, and can be widely used in the fields of medicine, medical devices, biological materials, tissue engineering, cosmetics, and the like.

(3) It is experimentally verified that the recombinant human type XVII collagen in the present disclosure has the same or better cell adhesion activity, cell migration-promoting activity, tissue repair-promoting activity, and hair follicle repair and regeneration-promoting activity compared to the commercial native human collagen, and can achieve the purpose of real product application.

(4) The recombinant human type XVII collagen in the present disclosure can undergo efficient secretory expression in the *P. pastoris* expression system, and is easily purified to obtain the high-purity collagen. The DNA sequence of the gene encoding the amino acid sequence is optimized, such that the constructed engineered strain can express the protein at a very high level, and a high yield of the protein can be obtained after high-density fermentation and expression. *P. pastoris* can be easily used for high-density fermentation and expression, and the strain screened out in the present disclosure can achieve the high-density and high-expression fermentation at a 500 L pilot scale, which provides the conditions for industrialized mass production.

(5) The host cell *P. pastoris* in the present disclosure can perform a post-translational modification on the expressed exogenous protein, such as glycosylation.

BRIEF DESCRIPTION OF THE DRAWINGS

FIG. 9 shows a mass spectrometry (MS) analysis result of an SDS-PAGE band of the collagen 170801 and a sequence alignment result thereof with the native human type XVII collagen shown in SEQ ID NO: 1.

FIG. 10 shows an MS analysis result of an SDS-PAGE band of the collagen 170802 and a sequence alignment result thereof with the native human type XVII collagen shown in SEQ ID NO: 1.

DETAILED DESCRIPTION OF THE EMBODIMENTS

Figure 1:
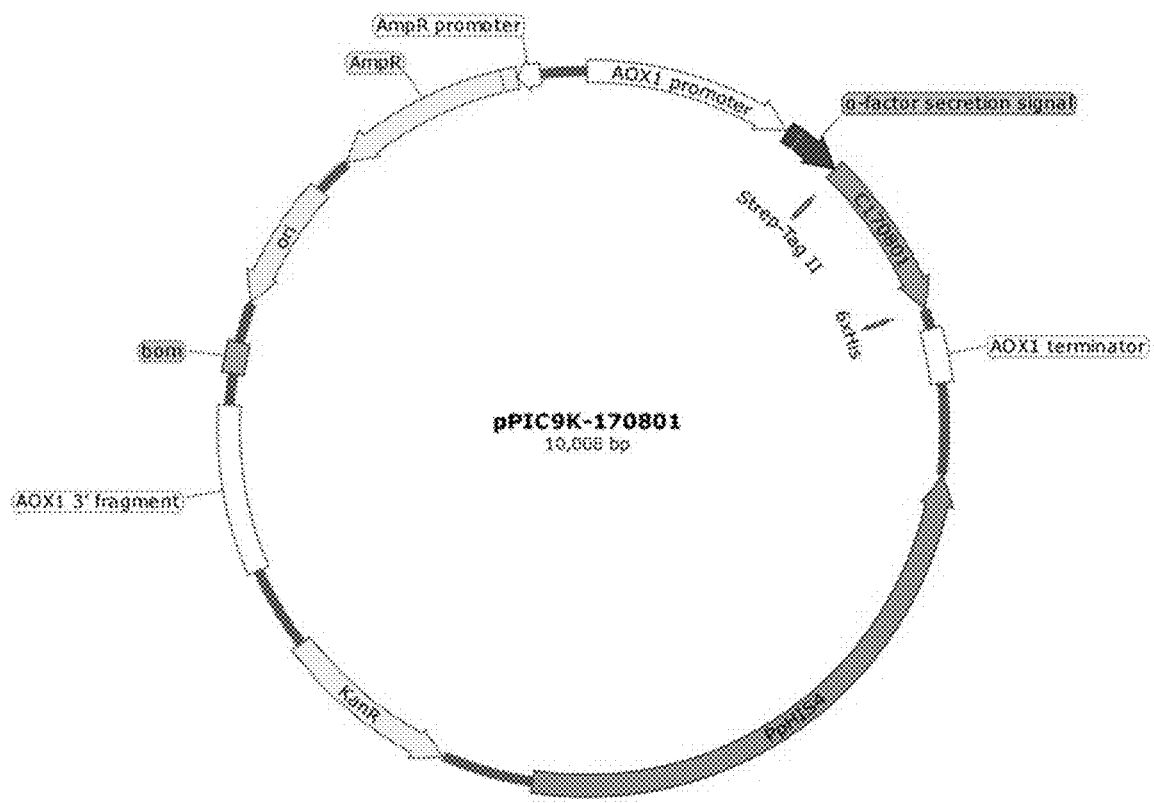
FIG. 1 is a map of the pPIC9K-170801 vector constructed in the present disclosure.

In order to make those skilled in the art better understand the technical solutions of the present disclosure, the preferred examples of the present disclosure are described in detail below, but the following examples do not limit the protection scope of the present disclosure.

In the examples of the present disclosure, those not described in detail are all implemented by a conventional molecular biology experimental method; and processes such as polymerase chain reaction (PCR), enzyme digestion, ligation, and codon optimization involved in the examples can all be understood and easily implemented by those skilled in the art according to product instructions or basic knowledge in the art, and thus will not be described in detail.

Example 1: Construction, Expression, and Identification of a Recombinant Human Type XVII Collagen (1) Design of an Amino Acid Sequence of the Recombinant Human Type XVII Collagen In the present disclosure, a sequence of the human type XVII collagen is optimized, and a specific sequence of the human type XVII collagen is as follows: a Uniprot Q9UMD9-1 sequence (www.uniprot.org) and an NCBI reference sequence Q9UMD9. 3 (www.ncbi.nlm.nih.gov), which are the same, as set forth in SEQ ID NO: 1.

SEQ ID NO: 1:
MDVTKKNKRDGTEVTERIVTETVTTRLTSLPPKGGTSNGYAKTASLGGGS

RLEKQSLTHGSSGYINSTGSTRGHASTSSYRRAHSPASTLPNSPGSTFER

KTHVTRHAYEGSSSGNSSPEYPRKEFASSSTRGRSQTRESEIRVRLQSAS

PSTRWTELDDVKRLLKGSRSASVSPTRNSSNTLPIPKKGTVETKIVTASS

QSVSGTYDATILDANLPSHVWSSTLPAGSSMGTYHNNMTTQSSSLLNTNA

YSAGSVFGVPNNMASCSPTLHPGLSTSSSVFGMQNNLAPSLTTLSHGTTT

TSTAYGVKKNMPQSPAAVNTGVSTSAACTTSVQSDDLLHKDCKFLILEKD

NTPAKKEMELLIMTKDSGKVFTASPASIAATSFSEDTLKKEKQAAYNADS

GLKAEANGDLKTVSTKGKTTTADIHSYGSSGGGGSGGGGGVGGAGGGPWG

PAPAWCPCGSCCSWWKWLLGLLLTWLLLLGLLFGLIALAEEVRKLKARVD

ELERIRRSILPYGDSMDRIEKDRLQGMAPAAGADLDKIGLHSDSQEELWM

FVRKKLMMEQENGNLRGSPGPKGDMGSPGPKGDRGFPGTPGIPGPLGHPG

PQGPKGQKGSVGDPGMEGPMGQRGREGPMGPRGEAGPPGSGEKGERGAAG

EPGPHGPPGVPGSVGPKGSSGSPGPQGPPGPVGLQGLRGEVGLPGVKGDK

GPMGPPGPKGDQGEKGPRGLTGEPGMRGLPGAVGEPGAKGAMGPAGPDGH

QGPRGEQGLTGMPGIRGPPGPSGDPGKPGLTGPQGPQGLPGTPGRPGIKG

EPGAPGKIVTSEGSSMLTVPGPPGPPGAMGPPGPPGAPGPAGPAGLPGHQ

EVLNLQGPPGPPGPRGPPGPSIPGPPGPRGPPGEGLPGPPGPPGSFLSNS

ETFLSGPPGPPGPPGPKGDQGPPGPRGHQGEQGLPGFSTSGSSSFGLNLQ

GPPGPPGPQGPKGDKGDPGVPGALGIPSGPSEGGSSSTMYVSGPPGPPGP

PGPPGSISSSGQEIQQYISEYMQSDSIRSYLSGVQGPPGPPGPPGPVTTI

TGETFDYSELASHVVSYLRTSGYGVSLFSSSISSSEDILAVLQRDDVRQYL

RQYLMGPRGPPGPPGASGDGSLLSLDYAELSSRILSYMSSSGISIGLPGP

PGPPGLPGTSYEELLSLLRGSEFRGIVGPPGPPGPPGIPGNVWSSISVED

LSSYLHTAGLSFIPGPPGPPGPPGPRGPPGVSGALATYAAENSDSFRSEL

ISYLTSPDVRSFIVGPPGPPGPQGPPGDSRLLSTDASHSRGSSSSSHSSS

VRRGSSYSSSMSTGGGGAGSLGAGGAFGEAAGDRGPYGTDIGPGGGYGAA

AEGGMYAGNGGLLGADFAGDLDYNELAVRVSESMQRQGLLQGMAYTVQGP

PGQPGPQGPPGISKVFSAYSNVTADLMDFFQTYGAIQGPPGQKGEMGTPG

PKGDRGPAGPPGHPGPPGPRGHKGEKGDKGDQVYAGRRRRRSIAVKP

The bold and underlined parts in the above sequence SEQ ID NO: 1 are sequences selected by the present disclosure, with 233 amino acids in total. The sequences selected by the present disclosure are obtained through optimization and screening of multiple helix region sequences of human type XVII collagen such as the 15th helix region, the carboxyl terminus region, and the middle region, and are combined to obtain a combined sequence. The combined sequence can undergo efficient secretory and soluble expression in eukaryotic host cells such as *P. pastoris*, and exhibits more excellent cell adhesion activity, cell migration-promoting activity, tissue regeneration-promoting activity, and hair follicle repair and regeneration-promoting activity than commercial native human collagen. Such a combined sequence enables the integration of functions of the respective region sequences, such that the respective region sequences are not expressed separately but expressed as a whole, which avoids the sequence singleness of the recombinant collagen and is highly innovative. In the present disclosure, the combined sequence is named 170801 and is specifically set forth in SEQ ID NO: 2, which is a preferred sequence of human type XVII collagen.

SEQ ID NO: 2:
GSPGPKGDMGSPGPKGDRGFPGTPGIPGPLGHPGPQGPKGQKGSVGDPGM

EGPGEKGERGAAGEPGPHGPPGVPGSVGPKGSSGSPGPQGPPGPVGLQGL

RGEVGLPGVKGDKGPMGPPGPKGDQGEKGPPGPPGPPGPKGDQGPPGPRG

HQGEQGLPGFSGPPGPPGPQGPKGDKGDPGVPGALGIPGPPGQKGEMGTP

GPKGDRGPAGPPGHPGPPGPRGHKGEKGDKGDQ

A DNA sequence encoding 170801 is set forth in SEQ ID NO: 6.

SEQ ID NO: 6:
GGTTCTCCTGGTCCAAAAGGTGACATGGGTTCTCCAGGTCCTAAAGGTGA

CAGAGGTTTTCCTGGTACTCCAGGTATTCCTGGTCCATTGGGTCATCCAG

GTCCTCAAGGTCCAAAAGGTCAAAAGGGTTCTGTTGGTGACCCTGGTATG

GAAGGTCCAGGTGAAAAGGGTGAAAGAGGTGCTGCTGGTGAACCTGGTCC

ACACGGTCCACCTGGTGTTCCAGGTTCTGTTGGTCCTAAGGGTTCTTCTG

GTTCTCCTGGTCCACAAGGTCCTCCTGGTCCAGTTGGTTTGCAAGGTTTG

AGAGGTGAAGTTGGTTTGCCAGGTGTTAAGGGTGACAAGGGTCCAATGGG

TCCTCCAGGTCCAAAAGGTGACCAAGGTGAAAAGGGTCCACCTGGTCCTC

CTGGTCCACCTGGTCCAAAGGGTGACCAAGGTCCTCCAGGTCCTAGAGGT

CATCAAGGTGAACAAGGTTTGCCTGGTTTTTCTGGTCCACCAGGTCCTCC

AGGTCCACAAGGTCCTAAAGGTGACAAAGGTGACCCAGGTGTTCCTGGTG

CTTTGGGTATTCCAGGTCCACCTGGTCAAAAAGGTGAAATGGGTACTCCA

GGTCCTAAGGGTGACAGAGGTCCAGCTGGTCCACCTGGTCATCCTGGTCC

ACCAGGTCCAAGAGGTCATAAGGGTGAAAAAGGTGACAAGGGTGACCAA

The collagen in the present disclosure has an amino acid sequence composed of n basic units connected in tandem, where 170801 is used as a basic unit, and n is an integer greater than or equal to 1.

When 170801 is used as a basic unit, if n is 2, the collagen has an amino acid sequence composed of 2 basic units 170801 connected in tandem, and the collagen has 466 amino acids in total, and is named 170802, and the amino acid sequence of the collagen is specifically set forth in SEQ ID NO: 3.

SEQ ID NO: 3:
GSPGPKGDMGSPGPKGDRGFPGTPGIPGPLGHPGPQGPKGQKGSVGDPGM

EGPGEKGERGAAGEPGPHGPPGVPGSVGPKGSSGSPGPQGPPGPVGLQGL

RGEVGLPGVKGDKGPMGPPGPKGDQGEKGPPGPPGPPGPKGDQGPPGPRG

HQGEQGLPGFSGPPGPPGPQGPKGDKGDPGVPGALGIPGPPGQKGEMGTP

-continued
GPKGDRGPAGPPGHPGPPGPRGHKGEKGDKGDQGSPGPKGDMGSPGPKGD

RGFPGTPGIPGPLGHPGPQGPKGQKGSVGDPGMEGPGEKGERGAAGEPGP

HGPPGVPGSVGPKGSSGSPGPQGPPGPVGLQGLRGEVGLPGVKGDKGPMG

PPGPKGDQGEKGPPGPPGPPGPKGDQGPPGPRGHQGEQGLPGFSGPPGPP

GPQGPKGDKGDPGVPGALGIPGPPGQKGEMGTPGPKGDRGPAGPPGHPGP

PGPRGHKGEKGDKGDQ

A DNA sequence encoding 170802 is set forth in SEQ ID NO: 7.

```
SEQ ID NO: 7:
GGTTCTCCAGGTCCTAAAGGTGACATGGGTTCTCCAGGTCCTAAGGGTGA

CAGAGGTTTTCCAGGTACTCCAGGTATTCCAGGTCCTTTGGGTCATCCAG

GTCCTCAAGGTCCTAAAGGTCAAAAAGGTTCTGTTGGTGACCCTGGTATG

GAAGGTCCTGGTGAAAAAGGTGAAAGAGGTGCTGCTGGTGAACCTGGTCC

ACACGGTCCTCCAGGTGTTCCTGGTTCTGTTGGTCCAAAAGGTTCTTCTG

GTTCTCCTGGTCCACAAGGTCCTCCAGGTCCTGTTGGTTTGCAAGGTTTG

AGAGGTGAAGTTGGTTTGCCAGGTGTTAAAGGTGACAAAGGTCCAATGGG

TCCTCCAGGTCCAAAGGGTGACCAAGGTGAAAAAGGTCCACCTGGTCCTC

CTGGTCCACCAGGTCCAAAAGGTGACCAAGGTCCACCTGGTCCAAGAGGT

CACCAAGGTGAACAAGGTTTGCCTGGTTTTTCTGGTCCTCCAGGTCCTCC

TGGTCCTCAAGGTCCAAAGGGTGACAAGGGTGACCCTGGTGTTCCAGGTG

CTTTGGGTATTCCTGGTCCTCCAGGTCAAAAGGGTGAGATGGGTACTCCT

GGTCCTAAGGGTGACAGAGGTCCAGCTGGTCCTCCTGGTCACCCAGGTCC

TCCTGGTCCTAGAGGTCATAAAGGTGAAAAAGGTGACAAGGGTGACCAAG

GTTCTCCAGGTCCAAAGGGTGACATGGGTTCTCCTGGTCCAAAAGGTGAC

AGAGGTTTCCCTGGTACTCCAGGTATTCCTGGTCCATTGGGTCACCCAGG

TCCACAAGGTCCAAAAGGTCAAAAAGGTTCTGTTGGTGACCCAGGTATGG

AAGGTCCAGGTGAAAAGGGTGAAAGAGGTGCTGCTGGTGAACCAGGTCCT

CATGGTCCACCAGGTGTTCCAGGTTCTGTTGGTCCAAAGGGTTCTTCTGG

TTCTCCAGGTCCACAAGGTCCTCCAGGTCCAGTTGGTTTGCAAGGTTTGA

GAGGTGAAGTTGGTTTGCCTGGTGTTAAGGGTGACAAAGGTCCTATGGGT

CCTCCTGGTCCTAAAGGTGACCAAGGTGAAAAGGGTCCACCAGGTCCTCC

AGGTCCACCTGGTCAAAAGGTGACCAAGGTCCACCAGGTCCTAGAGGTC

ATCAAGGTGAACAAGGTTTGCCAGGTTTTTCTGGTCCACCAGGTCCACCA

GGTCCTCAAGGTCCTAAGGGTGACAAAGGTGACCCAGGTGTTCCTGGTGC

TTTGGGTATTCCTGGTCCACCTGGTCAAAAGGGTGAAATGGGTACTCCTG

GTCCTAAAGGTGACAGAGGTCCTGCTGGTCCACCTGGTCATCCAGGTCCA

CCTGGTCCAAGAGGTCACAAAGGTGAAAAGGGTGACAAGGGTGACCAA
```

A function of the protein can only be realized through the orderly arrangement of amino acid residues of the protein. All innovative biological activities of the recombinant human type XVII collagen in the present disclosure are based on the amino acid sequence selected through optimization and screening, and a limited sequence modification or a specified percentage of homology (greater than 80%) may still achieve the same or similar biological activities.

Therefore, in the present disclosure, the collagen also includes an amino acid sequence undergoing a modification such as amino acid insertion, substitution, addition, or deletion to a predetermined extent based on SEQ ID NO: 2, or an amino acid sequence that has more than 80% homology with the amino acid sequence set forth in SEQ ID NO: 2, where either of the above amino acid sequences is used as a basic unit, and n basic units are connected in tandem to obtain the amino acid sequence of the collagen, where n is an integer greater than or equal to 1, and the basic units are identical or different if there are two or more basic units.

The homology mentioned in the present disclosure refers to an identity of sequences, which can be a direct quantitative relationship between two sequences, such as a percentage of identical and similar units, or a percentage of identical positions for which the nucleotide or amino acid residue is identical between two sequences. Homologous sequences may be different sequences obtained through divergent evolution from a common ancestor. The homology can be obtained through sequence information alignment by a conventional bioinformatics method.

The amino acid insertion refers to the insertion of amino acid residues at appropriate positions in an amino acid sequence such as a sequence set forth in SEQ ID NO: 2 or SEQ ID NO: 3, where the inserted amino acid residues are adjacent to each other or some of the inserted amino acid residues are adjacent to each other, or none of the inserted amino acid residues are adjacent to each other. The resulting protein has similar biological activities to collagens 170801 and 170802, including cell adhesion activity, cell migration-promoting activity, tissue regeneration-promoting activity, and hair follicle repair and regeneration-promoting activity.

The amino acid substitution refers to the substitution of one or more amino acid residues (including consecutive amino acid residues or non-consecutive amino acid residues) at a specified position in an amino acid sequence such as a sequence set forth in SEQ ID NO: 2 or SEQ ID NO: 3 with other amino acid residues. The resulting protein has similar biological activities to collagens 170801 and 170802, including cell adhesion activity, cell migration-promoting activity, tissue regeneration-promoting activity, and hair follicle repair and regeneration-promoting activity.

The amino acid addition refers to the addition of an amino acid to a C-terminus or N-terminus of an amino acid sequence such as a sequence set forth in SEQ ID NO: 2 or SEQ ID NO: 3. The resulting protein has similar biological activities to collagens 170801 and 170802, including cell adhesion activity, cell migration-promoting activity, tissue regeneration-promoting activity, and hair follicle repair and regeneration-promoting activity.

The amino acid deletion refers to the deletion of 1, 2, 3, or more amino acids from an amino acid sequence such as a sequence set forth in SEQ ID NO: 2 or SEQ ID NO: 3. The resulting protein has similar biological activities to collagens 170801 and 170802, including cell adhesion activity, cell migration-promoting activity, tissue regeneration-promoting activity, and hair follicle repair and regeneration-promoting activity.

The amino acids mentioned in the present disclosure may preferably be L-amino acids. One or more (such as 2 to 5, 2 to 4, or 2 to 3) amino acids in the polypeptide can also be replaced with D-amino acids, artificially-modified amino acids, naturally-occurring rare amino acids, and the like to improve the bioavailability, stability, and/or antiviral activity of the polypeptide. The D-amino acids refer to amino acids corresponding to L-amino acids that constitute proteins; the artificially-modified amino acids refer to common L-amino acids modified by methylation, phosphorylation, or the like that constitute proteins; and the naturally-occurring rare amino acids include uncommon amino acids that constitute proteins and amino acids that do not constitute proteins, such as 5-hydroxylysine, methylhistidine, gamma-aminobutyric acid (GABA), and homoserine.

(2) Optimization of Amino Acid Sequences and DNA Sequences for the Recombinant Human Type XVII Collagen In the present disclosure, DNA sequences for 170801 and 170802 are modified as follows: a DNA sequence encoding a Strep-Tag II added to an amino terminus of each amino acid sequence and a DNA sequence encoding a hexahistidine Tag added to a carboxyl terminus are added, such that obtained collagens have bispecific affinity purification tags, which enables the purification by affinity chromatography and the immunological antibody detection based on the two tag sequences. Specifically, based on the amino acid sequences of 170801 and 170802 and gene sequences encoding the same, calculation, splicing, recombination, and optimization are conducted in the codon bias of DNA sequences and the relevant optimization parameters during transcription and translation to synthesize DNA sequences that can be highly expressed in P. pastoris.

In the present disclosure, two termini of 170801 are separately modified by adding a DNA sequence encoding a Strep-Tag II to the amino terminus, and adding a DNA sequence encoding a hexahistidine Tag to the carboxyl terminus, and a protein with the tags is finally expressed, which has 249 amino acids in total. The optimized amino acid sequence of 170801 is set forth in SEQ ID NO: 4. Two termini of 170801 are separately modified by adding a DNA sequence encoding a Strep-Tag II to the amino terminus, and adding a DNA sequence encoding a hexahistidine Tag, a stop codon (TAA) and a Not I restriction site to the carboxyl terminus. The resulting DNA sequence is set forth in SEQ ID NO: 8.

SEQ ID NO: 4:
YVWSHPQFEKGSPGPKGDMGSPGPKGDRGFPGTPGIPGPLGHPGPQGPKG

QKGSVGDPGMEGPGEKGERGAAGEPGPHGPPGVPGSVGPKGSSGSPGPQG

PPGPVGLQGLRGEVGLPGVKGDKGPMGPPGPKGDQGEKGPPGPPGPPGPK

GDQGPPGPRGHQGEQGLPGFSGPPGPPGPQGPKGDKGDPGVPGALGIPGP

PGQKGEMGTPGPKGDRGPAGPPGHPGPPGPRGHKGEKGDKGDQHHHHHH

SEQ ID NO: 8:
TACGTATGGTCTCATCCACAATTCGAGAAGGGTTCTCCTGGTCCAAAAGG

TGACATGGGTTCTCCAGGTCCTAAAGGTGACAGAGGTTTTCCTGGTACTC

CAGGTATTCCTGGTCCATTGGGTCATCCAGGTCCTCAAGGTCCAAAAGGT

CAAAAGGGTTCTGTTGGTGACCCTGGTATGGAAGGTCCAGGTGAAAAGGG

TGAAAGAGGTGCTGCTGGTGAACCTGGTCCACACGGTCCACCTGGTGTTC

CAGGTTCTGTTGGTCCTAAGGGTTCTTCTGGTTCTCCTGGTCCACAAGGT

CCTCCTGGTCCAGTTGGTTTGCAAGGTTTGAGAGGTGAAGTTGGTTTGCC

AGGTGTTAAGGGTGACAAGGGTCCAATGGGTCCTCCAGGTCCAAAAGGTG

ACCAAGGTGAAAAGGGTCCACCTGGTCCTCCTGGTCCACCTGGTCCAAAG

GGTGACCAAGGTCCTCCAGGTCCTAGAGGTCATCAAGGTGAACAAGGTTT

GCCTGGTTTTTCTGGTCCACCAGGTCCTCCAGGTCCACAAGGTCCTAAAG

GTGACAAAGGTGACCCAGGTGTTCCTGGTGCTTTGGGTATTCCAGGTCCA

CCTGGTCAAAAAGGTGAAATGGGTACTCCAGGTCCTAAGGGTGACAGAGG

TCCAGCTGGTCCACCTGGTCATCCTGGTCCACCAGGTCCAAGAGGTCATA

AGGGTGAAAAAGGTGACAAGGGTGACCAACACCATCATCACCATCATTAA

GCGGCCGC

Similarly, two termini of 170802 are separately modified by adding a DNA sequence encoding a Strep-Tag II to the amino terminus, and adding a DNA sequence encoding a hexahistidine Tag to the carboxyl terminus, and a protein with the tags is finally expressed, which has 482 amino acids in total. The optimized amino acid sequence of 170802 is set forth in SEQ ID NO: 5. Two termini of 170802 are separately modified by adding a DNA sequence encoding a Strep-Tag II to the amino terminus, and adding a DNA sequence encoding a hexahistidine Tag, a stop codon (TAA) and a Not I restriction site to the carboxyl terminus. The resulting DNA sequence is set forth in SEQ ID NO: 9.

SEQ ID NO: 5:
YVWSHPQFEKGSPGPKGDMGSPGPKGDRGFPGTPGIPGPLGHPGPQGPKG

QKGSVGDPGMEGPGEKGERGAAGEPGPHGPPGVPGSVGPKGSSGSPGPQG

PPGPVGLQGLRGEVGLPGVKGDKGPMGPPGPKGDQGEKGPPGPPGPPGPK

GDQGPPGPRGHQGEQGLPGFSGPPGPPGPQGPKGDKGDPGVPGALGIPGP

PGQKGEMGTPGPKGDRGPAGPPGHPGPPGPRGHKGEKGDKGDQGSPGPKG

DMGSPGPKGDRGFPGTPGIPGPLGHPGPQGPKGQKGSVGDPGMEGPGEKG

ERGAAGEPGPHGPPGVPGSVGPKGSSGSPGPQGPPGPVGLQGLRGEVGLP

GVKGDKGPMGPPGPKGDQGEKGPPGPPGPPGPKGDQGPPGPRGHQGEQGL

PGFSGPPGPPGPQGPKGDKGDPGVPGALGIPGPPGQKGEMGTPGPKGDRG

PAGPPGHPGPPGPRGHKGEKGDKGDQHHHHHH

SEQ ID NO: 9:
TACGTATGGTCTCATCCTCAATTTGAAAAGGGTTCTCCAGGTCCTAAAGG

TGACATGGGTTCTCCAGGTCCTAAGGGTGACAGAGGTTTTCCAGGTACTC

CAGGTATTCCAGGTCCTTTGGGTCATCCAGGTCCTCAAGGTCCTAAAGGT

CAAAAAGGTTCTGTTGGTGACCCTGGTATGGAAGGTCCTGGTGAAAAAGG

TGAAAGAGGTGCTGCTGGTGAACCTGGTCCACACGGTCCTCCAGGTGTTC

CTGGTTCTGTTGGTCCAAAAGGTTCTTCTGGTTCTCCTGGTCCACAAGGT

CCTCCAGGTCCTGTTGGTTTGCAAGGTTTGAGAGGTGAAGTTGGTTTGCC

AGGTGTTAAAGGTGACAAAGGTCCAATGGGTCCTCCAGGTCCAAAGGGTG

ACCAAGGTGAAAAAGGTCCACCTGGTCCTCCTGGTCCACCAGGTCCAAAA

GGTGACCAAGGTCCACCTGGTCCAAGAGGTCACCAAGGTGAACAAGGTTT

GCCTGGTTTTTCTGGTCCTCCAGGTCCTCCTGGTCCTCAAGGTCCAAAGG

GTGACAAGGGTGACCCTGGTGTTCCAGGTGCTTTGGGTATTCCTGGTCCT

CCAGGTCAAAAGGGTGAGATGGGTACTCCTGGTCCTAAGGGTGACAGAGG

TCCAGCTGGTCCTCCTGGTCACCCAGGTCCTCCTGGTCCTAGAGGTCATA

AAGGTGAAAAAGGTGACAAGGGTGACCAAGGTTCTCCAGGTCCAAAGGGT

-continued
GACATGGGTTCTCCTGGTCCAAAAGGTGACAGAGGTTTCCCTGGTACTCC

AGGTATTCCTGGTCCATTGGGTCACCCAGGTCCACAAGGTCCAAAAGGTC

AAAAAGGTTCTGTTGGTGACCCAGGTATGGAAGGTCCAGGTGAAAAGGGT

GAAAGAGGTGCTGCTGGTGAACCAGGTCCTCATGGTCCACCAGGTGTTCC

AGGTTCTGTTGGTCCAAAGGGTTCTTCTGGTTCTCCAGGTCCACAAGGTC

CTCCAGGTCCAGTTGGTTTGCAAGGTTTGAGAGGTGAAGTTGGTTTGCCT

GGTGTTAAGGGTGACAAAGGTCCTATGGGTCCTCCTGGTCCTAAAGGTGA

CCAAGGTGAAAAGGGTCCACCAGGTCCTCCAGGTCCACCTGGTCCAAAAG

GTGACCAAGGTCCACCAGGTCCTAGAGGTCATCAAGGTGAACAAGGTTTG

CCAGGTTTTTCTGGTCCACCAGGTCCACCAGGTCCTCAAGGTCCTAAGGG

-continued
TGACAAAGGTGACCCAGGTGTTCCTGGTGCTTTGGGTATTCCTGGTCCAC

CTGGTCAAAAGGGTGAAATGGGTACTCCTGGTCCTAAAGGTGACAGAGGT

CCTGCTGGTCCACCTGGTCATCCAGGTCCACCTGGTCCAAGAGGTCACAA

AGGTGAAAAGGGTGACAAGGGTGACCAACACCATCACCATCATCATTAAG

CGGCCGC

In the present disclosure, a DNA sequence encoding the amino acid sequence of the full-length human type XVII collagen (that is, α1 chain of human type XVII collagen) (a restriction site EcoR I and a DNA sequence encoding a Strep-Tag II are added to the amino terminus, and a DNA sequence encoding a hexahistidine Tag, a stop codon (TAA), and a restriction site Not I are added to the carboxyl terminus) is set forth in SEQ ID NO: 10.

SEQ ID NO: 10:
GAATTCTGGAGTCATCCTCAATTCGAAAAAATGGATGTCACTAAAAAGAACAAG

AGAGACGGAACTGAGGTCACTGAGAGAATCGTTACCGAAACTGTCACCACAAGACT

TACTTCATTACCTCCAAAGGGTGGAACTTCTAATGGTTACGCAAAGACAGCATCATT

AGGAGGTGGTTCAAGACTTGAGAAACAATCCCTTACTCATGGTTCAAGTGGATACAT

AAATTCAACTGGTTCAACAAGAGGACATGCAAGTACTTCTTCTTATAGAAGAGCACA

TAGTCCAGCATCAACTTTGCCCAACTCTCCTGGTTCAACATTTGAGAGAAAAACTCA

TGTAACCAGACATGCCTATGAGGGTTCTAGTTCTGGTAATTCATCTCCAGAATACCC

TAGAAAAGAGTTTGCATCATCCTCAACTAGAGGTAGATCACAGACTAGAGAATCTG

AAATCAGAGTCAGATTACAATCAGCATCTCCTTCAACTAGATGGACTGAGTTAGACG

ACGTGAAAAGATTATTAAAGGGATCAAGAAGTGCAAGTGTTTCCCCTACAAGAAAT

TCTTCCAACACCCTTCCCATTCCTAAGAAAGGAACCGTTGAAACTAAAATCGTTACA

GCATCATCTCAGTCTGTATCCGGAACCTACGACGCTACCATTCTGGACGCCAACTTA

CCTTCTCATGTCTGGTCTTCAACTTTACCCGCAGGTTCCTCAATGGGAACTTACCACA

ATAACATGACTACTCAATCAAGTTCTCTTCTGAATACCAATGCATACTCAGCCGGTT

CCGTTTTTGGAGTCCCTAACAATATGGCCTCTTGCTCCCCAACTCTTCATCCAGGTCT

TTCAACCTCATCAAGTGTATTTGGTATGCAGAACAACTTAGCCCCTTCCTTGACAAC

CCTGTCTCATGGTACTACTACCACTAGTACAGCATATGGAGTCAAGAAGAACATGCC

ACAGTCACCTGCTGCCGTTAACACTGGAGTTTCAACATCTGCTGCCTGCACTACATC

TGTTCAATCAGATGATCTTCTGCATAAGGACTGCAAGTTTTTAATTTTAGAGAAAGA

CAATACCCCTGCCAAAAAGGAAATGGAGTTACTTATAATGACCAAAGATTCTGGTA

AAGTATTCACTGCTTCTCCCGCTAGTATCGCCGCAACTTCATTCTCTGAAGATACTTT

AAAGAAGGAAAAACAAGCCGCATACAACGCAGACTCAGGTTTAAAAGCAGAAGCA

AACGGTGACCTTAAAACAGTGTCAACTAAGGGAAAGACTACAACCGCAGACATCCA

TTCATATGGTTCTTCAGGTGGAGGAGGATCTGGAGGAGGTGGTGGAGTGGGAGGTG

CTGGAGGAGGTCCATGGGGTCCTGCACCTGCATGGTGCCCTTGCGGTTCTTGCTGCA

GTTGGTGGAAGTGGCTTCTGGGTTTATTATTAACTTGGCTGCTTTTACTGGGTCTTTT

ATTCGGTCTTATCGCATTAGCAGAAGAGGTCAGAAAACTTAAGGCCAGAGTTGATG

AGTTAGAGAGAATCAGAAGATCAATCCTTCCCTATGGAGACTCCATGGACAGAATC

GAAAAGGATAGACTTCAGGGTATGGCCCCTGCAGCAGGAGCTGATCTGGATAAAAT

-continued

```
CGGACTTCATTCAGATTCTCAAGAGGAATTATGGATGTTTGTTAGAAAGAAACTTAT
GATGGAGCAGGAGAACGGTAACCTGAGAGGTTCTCCTGGTCCAAAAGGAGATATGG
GTTCACCCGGTCCCAAAGGAGATAGAGGATTCCCTGGTACTCCAGGTATCCCCGGTC
CCCTGGGTCACCCTGGACCTCAAGGTCCTAAAGGTCAAAAGGGTTCTGTAGGAGATC
CAGGTATGGAGGGTCCCATGGGTCAGAGAGGTAGAGAAGGTCCCATGGGACCAAGA
GGTGAAGCTGGACCTCCCGGAAGTGGTGAAAAAGGAGAAAGAGGAGCAGCAGGAG
AACCTGGACCCCATGGACCTCCAGGAGTTCCTGGATCAGTCGGACCCAAAGGTTCAT
CCGGTTCTCCTGGACCTCAAGGTCCACCAGGACCCGTCGGATTGCAAGGATTGAGA
GGAGAAGTTGGACTTCCCGGAGTTAAGGGTGACAAGGGTCCTATGGGTCCTCCTGGT
CCAAAGGGAGATCAGGGTGAAAAGGGTCCTAGAGGTCTGACTGGTGAACCAGGAAT
GAGAGGACTTCCCGGTGCCGTGGGTGAACCCGGTGCAAAAGGAGCAATGGGTCCTG
CCGGTCCTGATGGACACCAGGGACCCAGAGGAGAGCAGGGATTAACAGGAATGCCT
GGTATCAGAGGTCCCCCAGGTCCCTCAGGAGACCCAGGAAAGCCAGGACTTACTGG
TCCCCAGGGTCCTCAAGGTCTGCCTGGAACTCCCGGAAGACCCGGAATCAAAGGTG
AACCAGGAGCCCCAGGAAAAATCGTTACTAGTGAAGGATCTTCAATGCTGACTGTG
CCAGGTCCACCTGGTCCTCCTGGAGCTATGGGTCCTCCCGGTCCCCCTGGAGCACCC
GGTCCTGCAGGTCCTGCCGGATTACCTGGACATCAGGAAGTCTTAAACCTGCAAGGT
CCACCAGGTCCTCCTGGTCCAAGAGGACCCCCTGGTCCTTCAATCCCTGGTCCACCT
GGACCTAGAGGTCCACCCGGAGAGGGACTTCCCGGACCACCAGGACCTCCTGGATC
ATTTCTGTCTAATTCTGAGACATTTCTTTCAGGACCTCCTGGTCCTCCCGGACCACCT
GGACCAAAAGGAGATCAGGGACCACCTGGTCCCAGAGGACATCAAGGAGAGCAGG
GTCTTCCAGGTTTCTCTACTTCTGGATCATCATCATTTGGTCTTAATCTTCAAGGTCCT
CCTGGACCCCCAGGACCACAGGGACCCAAGGGTGACAAGGGAGACCCTGGAGTCCC
AGGTGCACTGGGAATCCCTTCAGGTCCTTCAGAAGGTGGTTCATCTTCAACCATGTA
TGTGTCTGGACCCCCAGGACCTCCCGGACCTCCAGGTCCTCCTGGTTCAATCTCTTCT
TCTGGTCAAGAAATTCAGCAGTATATTTCTGAGTACATGCAATCTGACTCTATTAGA
AGTTATTTGTCTGGTGTGCAGGGTCCACCAGGTCCTCCAGGTCCCCCTGGACCAGTC
ACTACTATCACTGGAGAGACATTTGATTATAGTGAATTAGCATCACACGTCGTTTCT
TATCTGAGAACTTCAGGTTATGGTGTTTCATTATTTTCCTCCTCAATCTCTTCAGAAG
ACATCTTAGCCGTACTGCAGAGAGATGATGTAAGACAGTACCTTAGACAATACTTGA
TGGGTCCAAGAGGACCACCAGGTCCACCCGGTGCATCAGGAGACGGATCATTATTA
TCTTTGGATTACGCTGAATTATCATCAAGAATCCTTAGTTACATGTCCTCTTCTGGTA
TCTCCATAGGTCTGCCCGGTCCTCCTGGTCCTCCCGGACTTCCTGGTACTTCTTACGA
AGAGCTTCTGTCACTTTTAAGAGGATCTGAGTTTAGAGGTATAGTTGGTCCCCCAGG
ACCTCCAGGTCCTCCAGGTATCCCAGGTAACGTGTGGTCATCTATCTCAGTTGAGGA
TCTTTCATCTTATCTTCACACCGCCGGATTGTCCTTTATACCTGGTCCTCCAGGACCC
CCTGGACCTCCTGGACCCAGAGGTCCTCCAGGAGTATCCGGTGCTTTAGCAACTTAT
GCAGCAGAAAACTCCGATTCTTTTAGATCAGAATTGATCTCCTACCTTACTTCTCCTG
ATGTTAGATCATTCATCGTCGGACCTCCAGGACCACCTGGACCTCAAGGACCTCCTG
GAGATTCAAGATTACTGAGTACAGATGCATCACATTCAAGAGGTTCAAGTTCTTCTT
```

```
                                    -continued
CTCACTCCTCTTCTGTTAGAAGAGGATCATCATATTCATCAAGTATGTCAACTGGTG

GAGGAGGAGCTGGTTCATTGGGTGCCGGAGGTGCATTTGGTGAGGCCGCTGGTGAC

AGAGGACCTTATGGTACTGACATTGGACCTGGTGGAGGTTATGGTGCAGCAGCAGA

AGGTGGAATGTATGCTGGTAATGGAGGTTTACTGGGAGCCGACTTTGCCGGAGACCT

GGACTACAACGAGTTAGCTGTTAGAGTGTCAGAGTCAATGCAGAGACAAGGATTAT

TACAGGGTATGGCTTATACAGTTCAGGGACCCCCAGGTCAGCCAGGTCCTCAAGGA

CCCCCTGGTATTTCAAAAGTCTTCTCCGCTTATTCTAACGTTACTGCAGACCTGATGG

ATTTCTTCCAGACTTACGGTGCCATCCAAGGTCCTCCAGGACAGAAGGGTGAAATGG

GAACTCCCGGTCCCAAGGGTGACAGAGGTCCTGCAGGACCTCCTGGTCACCCTGGA

CCACCTGGACCTAGAGGACACAAAGGTGAGAAGGGTGACAAGGGAGACCAGGTTT

ACGCAGGAAGAAGAAGAAGAAGAAGTATTGCCGTCAAGCCTCACCATCACCATCAT

CACTAAGCGGCCGC
```

(3) Synthesis of DNA Sequences and Construction of Recombinant Expression Vectors In the present disclosure, the optimized sequences set forth in SEQ ID NO: 8, SEQ ID NO: 9, and SEQ ID NO: 10 were synthesized by Nanjing Genscript Biotechnology Co., Ltd., and the three gene fragments were denoted as pUC57-170801, pUC57-170802, and pUC57-col17a1. The synthesized gene fragments set forth in SEQ ID NO: 8 and SEQ ID NO: 9 were subjected to double enzyme digestion with SnaB I and Not I, and target gene fragments obtained after the enzyme digestion were ligated into a pPIC9K empty vector (purchased from Thermo Fisher Scientific) undergoing the same double enzyme digestion. The synthesized gene fragment set forth in SEQ ID NO: 10 was subjected to double enzyme digestion with EcoR I and Not I, and target fragments obtained after the enzyme digestion were ligated into a pPIC9K empty vector undergoing the same double enzyme digestion, which served as a control.

Step a. Amplification of the target genes and expression vector: The fragments of pUC57-170801, pUC57-170802, and pUC57-col17a1 and the plasmid of pPIC9K empty vector were extracted with a plasmid mini kit (purchased from Sangon Biotech (Shanghai) Co., Ltd.), and specific operations were conducted according to instructions of the kit.

Step b. The target gene fragments and the plasmid of pPIC9K vector obtained in step a were subjected to double enzyme digestion at 37° C. for 30 min. An enzyme digestion reaction system was as follows (the QuickCut™ restriction enzymes used were purchased from Dalian TaKaRa, and an enzyme digestion process was conducted according to instructions):

| Plasmid | 3 μg |
|---|---|
| 10 × H buffer | 5 μL |
| EcoRI/SnaB I | 10 U |
| NotI | 10 U |
| Sterile water | Making up to 50 μL |

The obtained target gene fragments and vector fragments were purified with a PCR product purification kit purchased from Dalian TaKaRa (specific operations were conducted according to instructions of the kit). Target gene fragments and linearized vector pPIC9K fragments obtained after the double enzyme digestion were recovered and subjected to ligation at 16° C. for 30 min with a Solution I ligation kit (purchased from Dalian TaKaRa), such that the target gene fragments were accurately inserted into a reading frame of the secretory vector carrying a secretion signal α-factor. A ligation reaction system was as follows (according to instructions of the ligation kit):

| Linearized pPIC9K fragments | 2 μL |
|---|---|
| Target gene fragments | 3 μL |
| Solution I ligation reagent | 5 μL |

Figure 2:
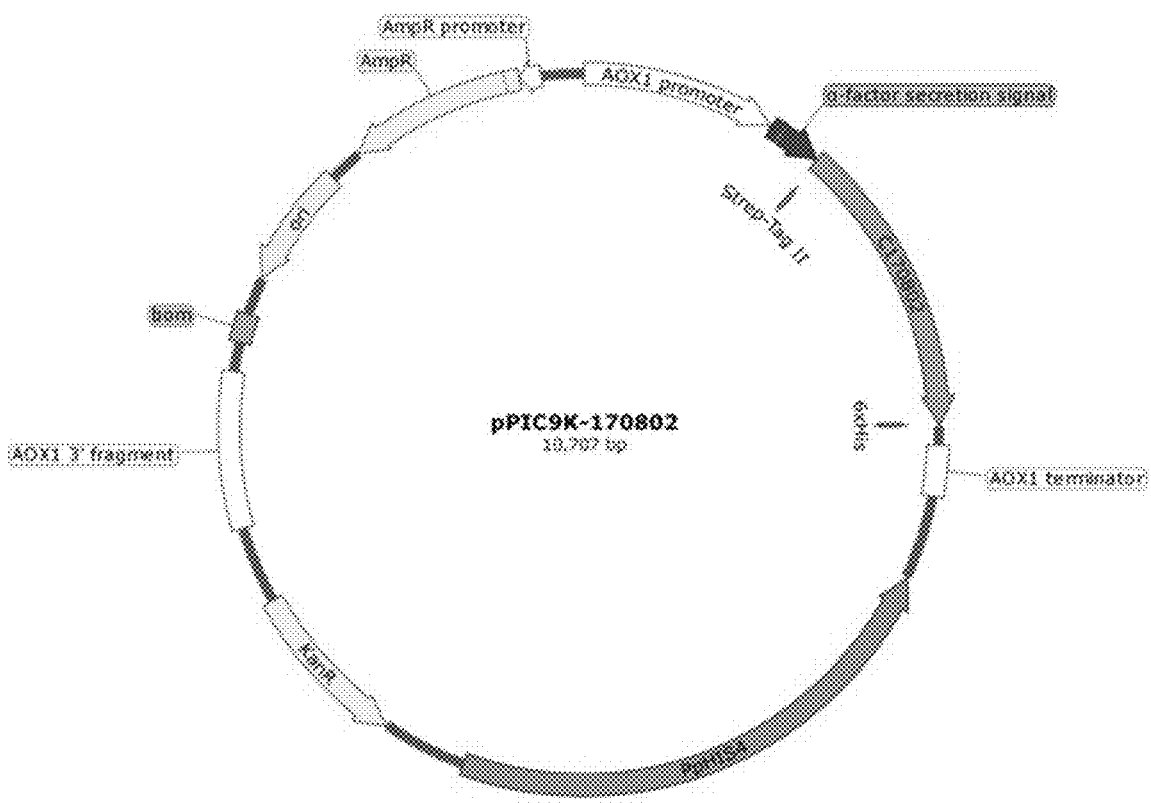
FIG. 2 is a map of the pPIC9K-170802 vector constructed in the present disclosure.
Figure 3:
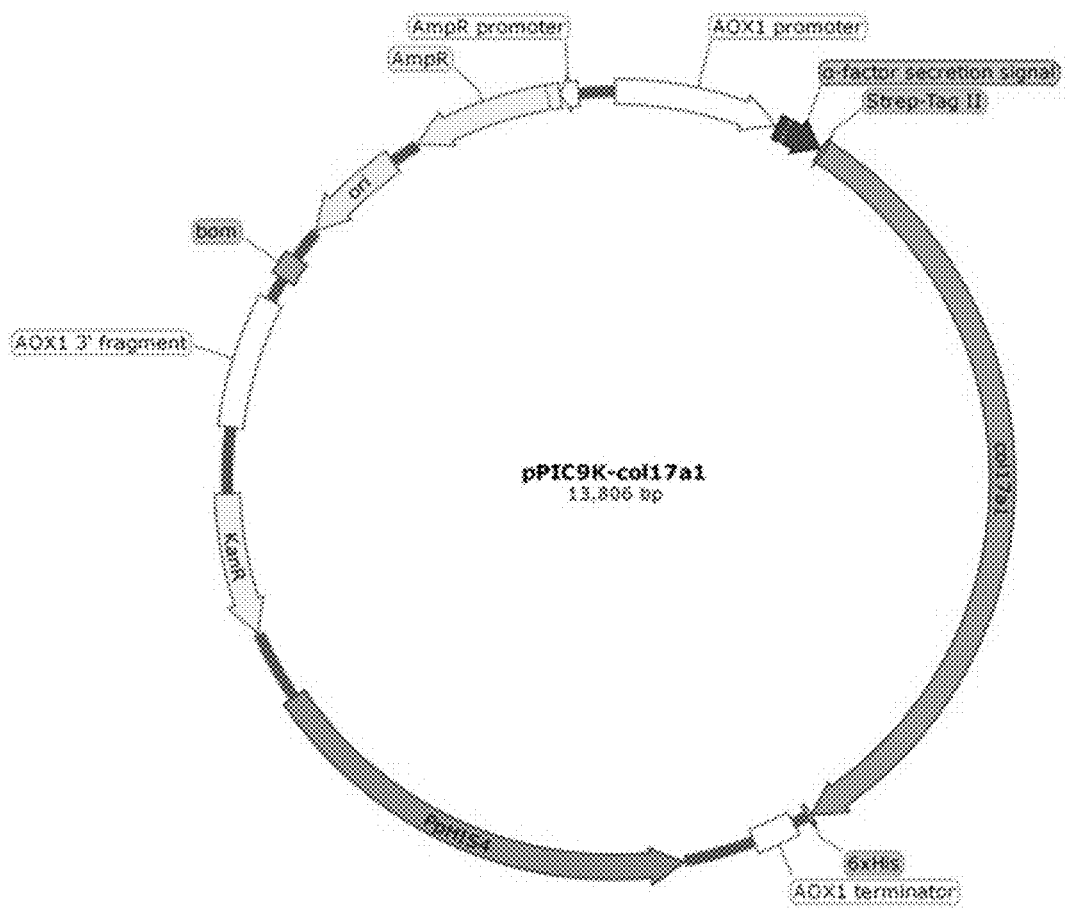
FIG. 3 is a map of the pPIC9K-col17a1 vector constructed in the present disclosure.

A ligation product was transformed into competent *E. coli* DH5α (purchased from Sangon Biotech (Shanghai) Co., Ltd.), positive clones were screened on an LB resistant plate with Amp, the colony PCR verification was conducted, and the recombinant plasmid was extracted for sequencing (which was entrusted to Sangon Biotech (Shanghai) Co., Ltd.). Positive sequencing results indicated that the recombinant expression vectors pPIC9K-170801, pPIC9K-170802, and pPIC9K-col17a1 were successfully constructed in this example, and relevant plasmid maps were respectively shown in FIG. 1, FIG. 2, and FIG. 3.

(4) Construction of Recombinant Engineered Strains and Screening of the Engineered Strains 10 μg of each of the recombinant expression vector plasmids obtained in step (3) was digested overnight at 37° C. with SacI (the enzyme digestion kit was purchased from Dalian TaKaRa, and specific operations were conducted according to instructions of the kit) for linearization, and then a PCR product purification kit (purchased from Sangon Biotech (Shanghai) Co., Ltd.) was used to recover the linearized plasmid, with a recovery volume controlled at about 10 μL.

The linearized plasmid was electrotransformed into competent cells of an empty host *P. pastoris* strain GS115 (purchased from China Center of Industrial Culture Collection (CICC)), an electrotransformed bacterial suspension was coated on an MD plate with 100 μL to 200 μL for each plate, and the plate was allowed to stand at room temperature for 10 min and invertedly incubated at 30° C. for 2 d to 5 d until single colonies (positive transformant) appeared.

2 mL of sterile double-distilled water (DDW) was added to a surface of the MD plate, then His⁺ transformants (positive transformants) on the surface of the plate were gently scraped off with a sterile triangular spreader, transferred to a 50 mL centrifuge tube, and diluted with sterile DDW to obtain a bacterial suspension, the bacterial suspension with $10^5$ cells was coated on a YPD plate with 0.5 mg/mL G418, and the plate was inverted and incubated at 30° C. for 3 d to 4 d until single colonies appeared. Colonies were picked from the YPD plate and added to a sterile 96-well plate (with 200 µL of YPD in each well), and the resulting mixture in each well was thoroughly mixed and incubated at 30° C. for 48 h; the resulting bacterial suspension in each well was thoroughly mixed, and 10 µL of the bacterial suspension was taken, added to a second sterile 96-well plate, and then incubated at 30° C. for 24 h; the resulting bacterial suspension in each well was thoroughly mixed, and 10 µL of the bacterial suspension was taken, added to a third sterile 96-well plate, and then incubated at 30° C. for 24 h; and 1 µL was taken from the third 96-well plate, and spotted on each of YPD plates containing 1.0 mg/mL and 4 mg/mL G418, and further incubated at 30° C. for 96 h to 120 h. If *P. pastoris* transformants can grow on a plate with high G418 concentration, it indicates that the transformants carry multiple copies of the target gene, that is, the multiple recombinant fragments have been introduced into *P. pastoris* and have been integrated into the chromosome of *P. pastoris* through homologous recombination. After the screening in this step, a recombinant *P. pastoris* engineered strain with high copy and high expression was obtained.

The three constructed engineered strain samples respectively carrying pPIC9K-col17a1, pPIC9K-170801, and pPIC9K-170802 were sent to the China General Microbiological Culture Collection Center (CGMCC) at No. 1, West Beichen Road, Chaoyang District, Beijing, China, with accession numbers of CGMCC No. 18659, CGMCC No. 20626, and CGMCC No. 20627, respectively, where the CGMCC No. 18659 was deposited on Oct. 10, 2019, and the CGMCC No. 20626 and CGMCC No. 20627 were deposited on Sep. 9, 2020, and the strains all had a taxonomic name of *Pichia pastoris*.

(5) Inducible Expression and Identification of Recombinant Collagen

Single colonies were picked from each of the YPD plates with 1.0 mg/mL and 4 mg/mL G418 in step (4), placed in a 100 mL erlenmeyer flask with 10 mL of a BMGY medium, and cultivated at 28° C. to 30° C. and 220 rpm until $OD_{600}$ was 2 to 6 (16 h to 18 h). The resulting bacterial suspension was centrifuged at 1,500 g to 3,000 g for 5 min at room temperature to collect bacterial cells, and the bacterial cells were resuspended in a BMMY medium such that $OD_{600}$ was about 2, and then cultivated on a shaker at 28° C. to 30° C. and 220 rpm for 3 d, during which 100% methanol was added to the medium every 24 h to a final concentration of 1.0%. 1 mL of a bacterial suspension sample was collected at different time points (≥24 h, if necessary, 24 h, 48 h, 72 h, and 96 h), placed in a 1.5 mL EP tube, and centrifuged at a maximum speed for 2 min to 3 min, and the resulting expression supernatant and bacterial cells were separately collected. The bacterial cells were lysed through disruption with glass beads (purchased from Sangon Biotech (Shanghai) Co., Ltd.) using a lysis buffer (1 mM PMSF, 10 mM Tris, pH 7.4), and the resulting lysate was centrifuged at 12,000 g and 4° C. for 5 min to obtain an intracellular lysis supernatant and a precipitate, the intracellular lysate supernatant was collected, and 8 M urea was added to the precipitate and the resulting mixture was shaken for dissolution. An expression level of the target protein and an optimal harvest time of the bacterial suspension were analyzed. The samples to be tested were stored at −80° C. for later use.

A 5× loading buffer (250 mM Tris-HCl, pH 6.8, 10% SDS, 0.5% bromophenol blue (BPB), 50% glycerin, and 5% β-mercaptoethanol) was added to each of the collected expression supernatant, intracellular lysis supernatant, and intracellular precipitate solution, and the resulting mixture was heated in a metal bath at 100° C. for 10 min and then subjected to SDS-PAGE. Because the expressed target protein included a Srtep-Tag II at an amino terminus and a hexahistidine tag at a carboxyl terminus, Western Blot was conducted with an anti-Srtep-Tag II antibody and an anti-hexahistidine Tag antibody (purchased from Nanjing Genscript Biotechnology Co., Ltd.).

Figure 4:
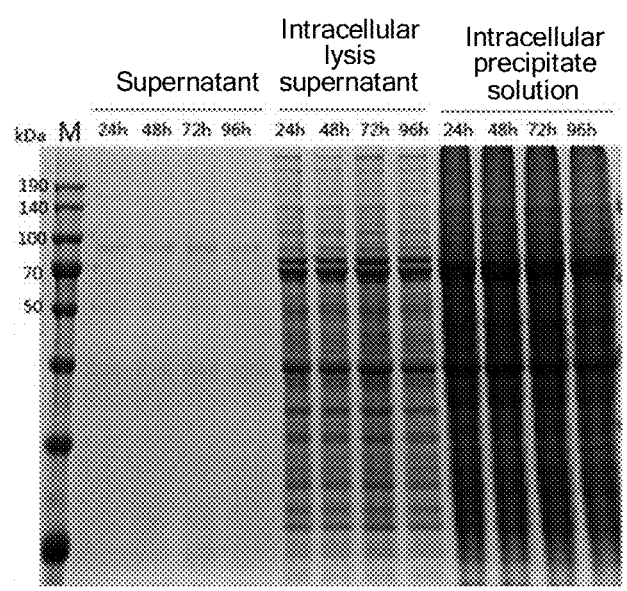
FIG. 4 shows an SDS-PAGE result of the expression of a α1 chain of the recombinant full-length human type XVII collagen, with an apparent molecular weight (AMW) of about 180 kDa.

Expression and Identification of a α1 Chain of a Recombinant Full-Length Human Type XVII Collagen:

It can be seen from the SDS-PAGE result in FIG. 4 that there was no expected target band (with an AMW of about 180 kDa) in the expression supernatant.

Figure 5:
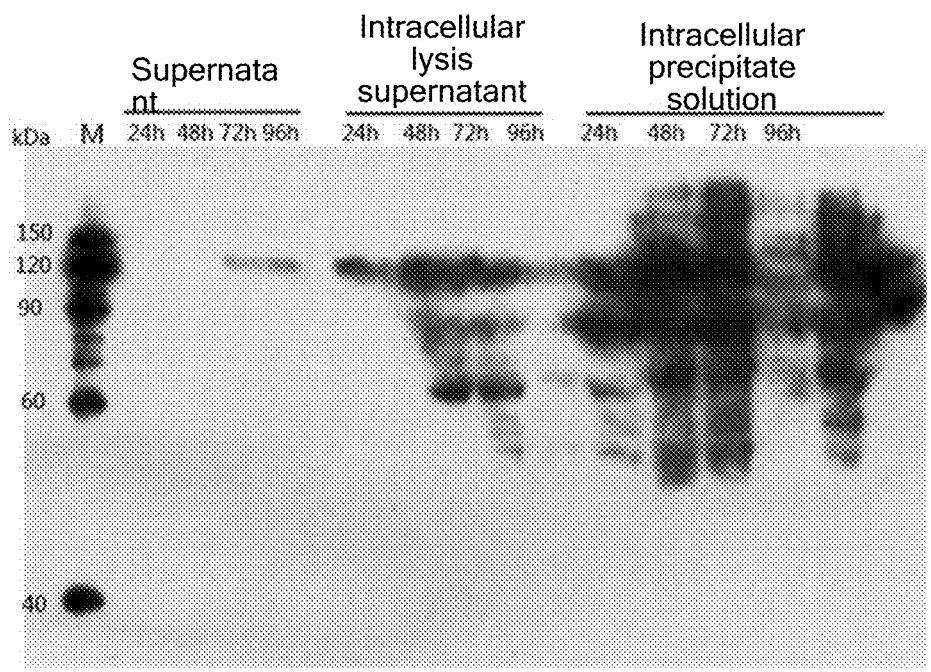
FIG. 5 shows a Western Blot result of the α1 chain of the recombinant full-length human type XVII collagen, where the Western Blot is conducted with an anti-His tag antibody.

Western Blot was conducted with an anti-hexahistidine Tag antibody, and a result was shown in FIG. 5. It was found that only a very small amount of the degraded target protein (an AMW was smaller than the expected one, and was about 120 kDa) was detected in the expression supernatant, and the degraded target protein appeared after a long time of inducible expression; there was a large amount of the degraded target protein in the intracellular lysis supernatant, and an AMW of the degraded target protein was smaller than the expected one and was about 120 kDa (which was consistent with an AMW of the extracellular domain of human type XVII collagen); and only the intracellular precipitate solution included the target protein with the expected AMW (180 kDa). The experimental results show that, as a transmembrane collagen, the protein should be fixed on an intracellular membrane system, and can fall off and be dissolved intracellularly only after being degraded; and the degraded target protein detected in the expression supernatant is most likely released into the expression supernatant after the lysis of cells that have died during the long-term cultivation. In either of the above cases, the full-length recombinant human type XVII collagen cannot be efficiently secreted extracellularly from *P. pastoris*.

Figure 6:
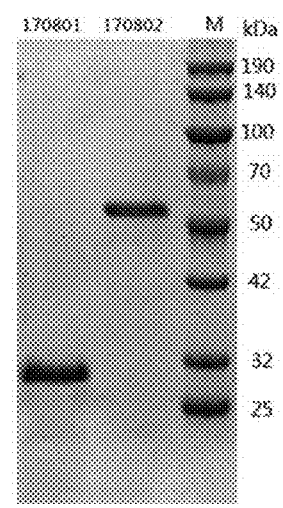
FIG. 6 shows SDS-PAGE results of expression supernatants of engineered bacteria expressing collagens 170801 and 170802 after 24 h of induction.

Expression and Identification of Collagens 170801 and 170802:

FIG. 6 shows SDS-PAGE results of expression supernatants of engineered bacteria expressing collagens 170801 and 170802 after 24 h of induction. As shown in FIG. 6, the collagens 170801 and 170802 can undergo efficient secretory expression in extracellular culture supernatants after 24 h of induction; and the 170801 has an AMW of about 30 kDa and the 170802 has an AMW of about 52 kDa.

Figure 7:
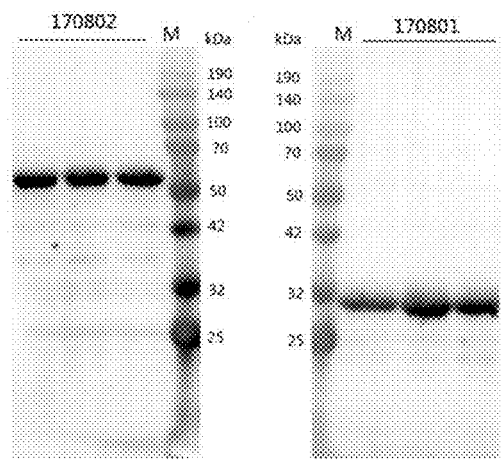
FIG. 7 shows Western Blot results of expression supernatants of engineered bacteria expressing collagens 170801 and 170802 after 24 h of induction, where the Western Blot is conducted with an anti-His tag antibody.
Figure 8:
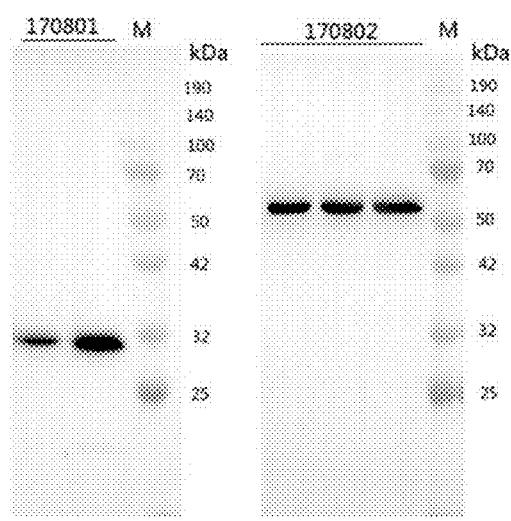
FIG. 8 shows Western Blot results of expression supernatants of engineered bacteria expressing collagens 170801 and 170802 after 24 h of induction, where the Western Blot is conducted with an anti-Strep-Tag II antibody.

FIG. 7 shows Western Blot results of expression supernatants of engineered bacteria expressing collagens 170801 and 170802 after 24 h of induction (Anti-His, the antibody is purchased from Sangon Biotech (Shanghai) Co., Ltd., and is a mouse anti-His monoclonal antibody (mAb), with Item No. D199987). FIG. 8 shows Western Blot results of expression supernatants of engineered bacteria expressing collagens 170801 and 170802 after 24 h of induction (Anti-Strep-Tag II, the antibody is purchased from Nanjing Genscript Biotechnology Co., Ltd., and is a rabbit anti-Strep-Tag polyclonal antibody (pAb), with Item No. A00626). It can be seen from the results in FIG. 7 and FIG. 8 (enhanced chemiluminescence (ECL) color development, the fully automatic chemiluminescence image analysis system Tanon 5200 integrates protein molecular mass markers into images) that the Srtep-Tag II tag at the amino terminus and the hexahistidine tag at the carboxyl terminus can be detected, and a size of the target band is the same as the AMW in SDS-PAGE, indicating that the recombinant human type XVII collagens 170801 and 170802 successfully undergo efficient secretory expression.

Figure 9:
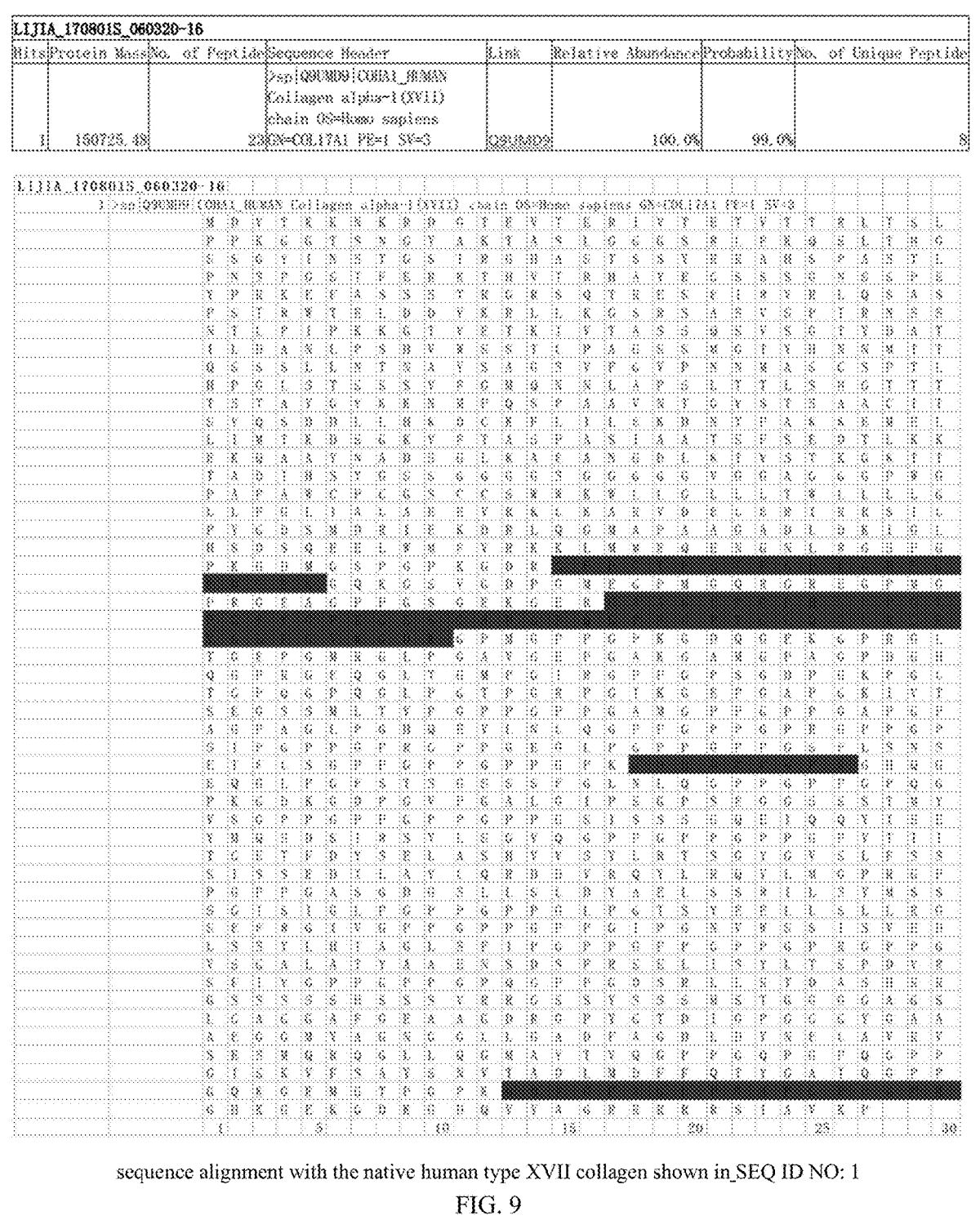
Figure 10:
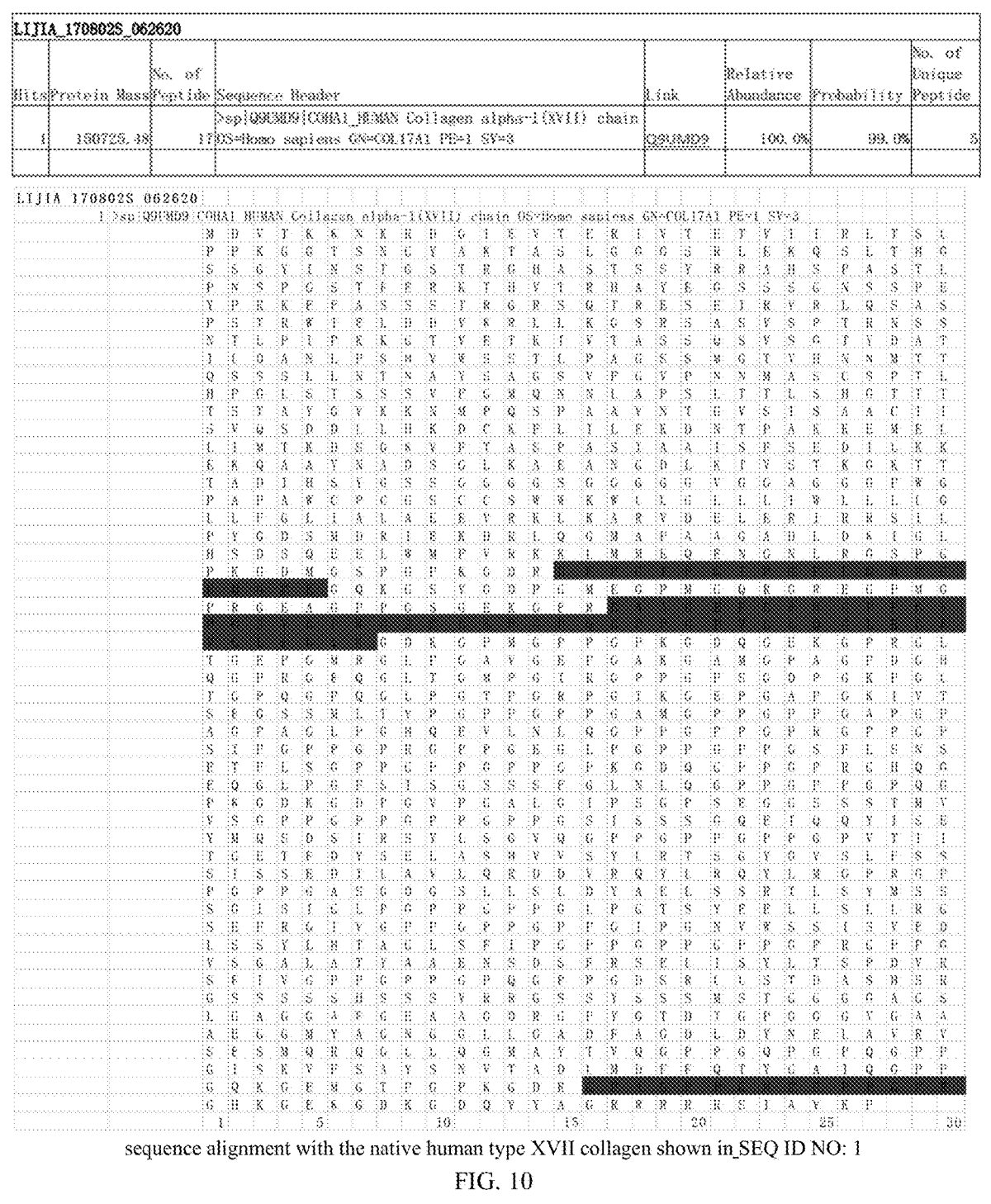

Bands of proteins resulting from inducible expression were recovered and digested with trypsin, peptides obtained after trypsin enzymolysis of the recombinant collagens were tested by Nano-HPLC-MS/MS (which was entrusted to Suzhou ProtTech Inc.), and the detected peptides were subjected to sequence alignment (Uniprot database). Results were shown in FIG. 9 and FIG. 10, and it can be seen that the peptides detected after the collagens 170801 and 170802 were enzymatically hydrolyzed were relevant regions of the human type XVII collagen sequences selected during the selection and design of amino acid sequences, indicating that the collagens 170801 and 170802 were successfully expressed.

Example 2: Pilot Fermentation of Genetically-Engineered Bacteria and Protein Purification (1) Pilot Fermentation The constructed engineered bacteria carrying pPIC9K-170801 and pPIC9K-170802 were each subjected to 50 L to 500 L linked pilot fermentation to obtain a fermentation broth with the recombinant human type XVII collagen, thereby realizing the large-scale expression and production of the recombinant human type XVII collagens 170801 and 170802.

A seed medium YPG (formula: yeast powder: 10 g/L, yeast peptone FP102: 20 g/L, and anhydrous glycerin: 10 g/L); a fermentation medium (formula: $NH_4H_2PO_4$: 190.4 g/L, $KH_2PO_4$: 10.06 g/L, $CaSO_4 \cdot 2H_2O$: 1.18 g/L, $K_2SO_4$: 18.2 g/L, $MgSO_4 \cdot 7H_2O$: 14.9 g/L, and glycerin: 40 g/L); a feed medium (50% W/V glycerin, with 12 mL of $PTM_1$ per liter); and an induction medium (100% methanol, with 12 mL of $PTM_1$ per liter) were adopted. The $PTM_1$ was filtered through a 0.22 μm filter membrane for sterilization and stored at 4° C. The fermentation medium was sterilized at a high temperature and cooled to room temperature, then $PTM_1$ was added, and a pH was adjusted to 5.0 with ammonia water.

The batch-cultivation and inducible expression of the constructed engineered strains were conducted as follows.

The fed-batch cultivation was conducted at 30° C. The constructed engineered bacteria were inoculated into a 2 L shake flask filled with the seed medium YPG and cultivated at 220 rpm and 30° C. for 24 h; the resulting bacterial suspension was inoculated at an inoculum size of 10% into a 50 L seed fermentation tank filled with the fermentation medium such that $OD_{600}$ was 5 after the inoculation, and the expanded cultivation was conducted at a stirring speed of 200 r/min to 600 r/min, an air flux of 2 VVM, and dissolved oxygen (DO) of greater than or equal to 30% until a carbon source was exhausted; and the resulting bacterial suspension was transferred to a 500 L fermentation tank filled with the fermentation medium, and the fermentation cultivation was conducted at a stirring speed of 150 r/min to 500 r/min, a tank pressure of 0 MPa to 0.05 MPa, an air flux of 1 VVM, and DO of greater than or equal to 30%. During the fermentation cultivation, when the DO was increased, the feed medium was fed at a flow to maintain DO≥30%, and when $OD_{600}$ grew to 190 to 210, the feeding was stopped, and when the DO was increased to be greater than or equal to 70%, the induction medium was fed, the stirring speed, air flux, tank pressure, and feeding flow were adjusted to make DO greater than or equal to 30%, and the inducible expression was conducted for 40 h to 72 h. When a protein concentration measured by a UV meter did not increase significantly or decreased, the resulting fermentation broth was discharged.

UV protein quantification formula: $C(mg/mL)=0.144*(A215-A225), A215<1.5$.

Figure 11:
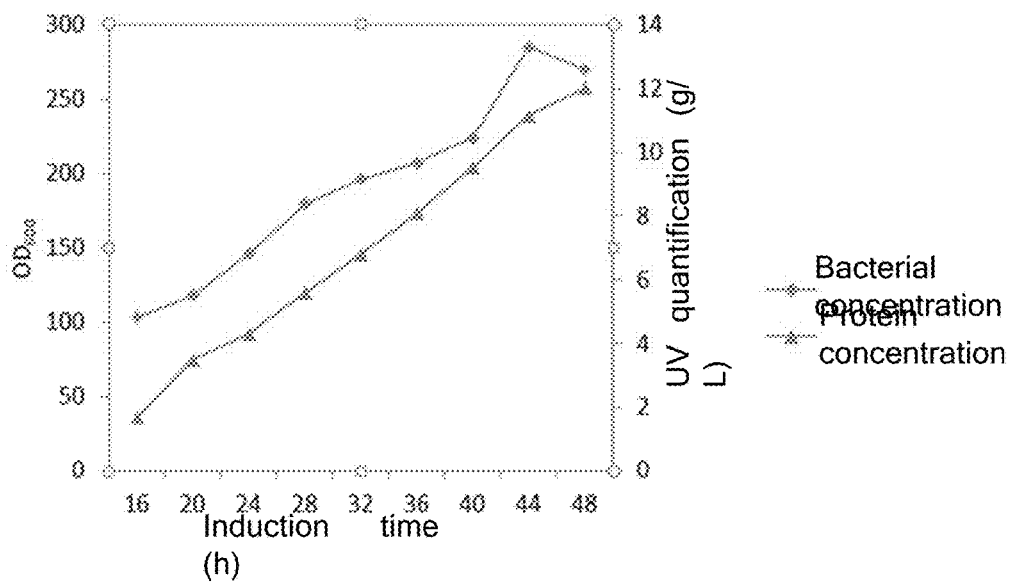
FIG. 11 shows a bacterial growth curve and a collagen expression curve of the 171801 collagen-expressing engineered bacterium in a 500 L pilot fermentation tank.
Figure 12:
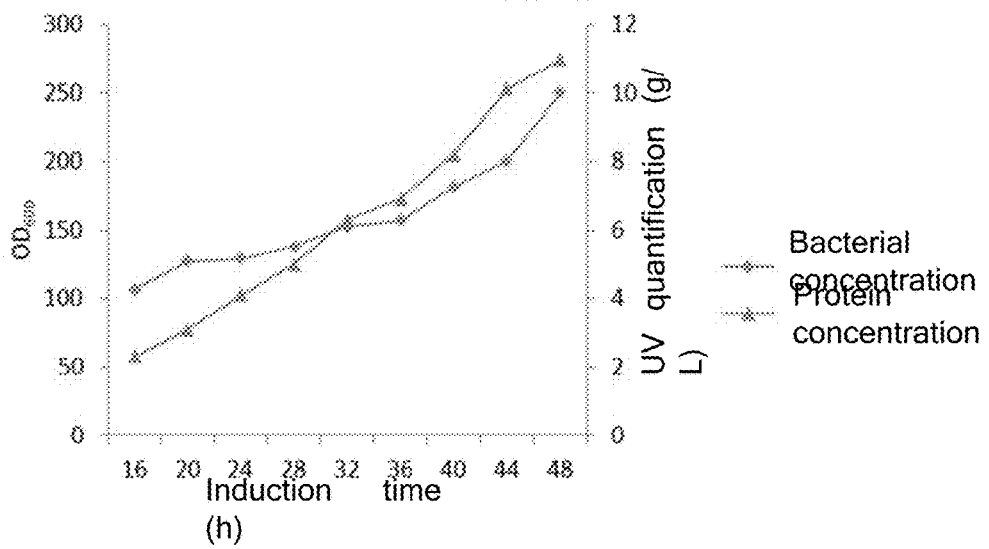
FIG. 12 shows a bacterial growth curve and a collagen expression curve of the 171802 collagen-expressing engineered bacterium in a 500 L pilot fermentation tank.

After the high-density pilot fermentation of the constructed engineered bacteria, it was found that, after induction for 48 h, a bacterial concentration ($OD_{600}$) could reach 250 or higher, a bacterial wet weight could reach about 300 g/L, and a protein concentration in a fermentation broth was greater than 10 g/L (UV quantification). The results were shown in FIG. 11 and FIG. 12. It can be seen from FIG. 11 that the engineered bacteria of 171801 grew well; and after induction for 48 h, a bacterial concentration ($OD_{600}$) could reach 270, a bacterial wet weight could reach 355 g/L, and a protein concentration in a fermentation broth could reach 12 g/L (UV quantification). It can be seen from FIG. 12 that the engineered bacteria of 171802 grew well; and after induction for 48 h, a bacterial concentration ($OD_{600}$) could reach 250, a bacterial wet weight could reach 293 g/L, and a protein concentration in a fermentation broth could reach 11 g/L (UV quantification).

(2) Purification

Buffers used in this example were as follows:
buffer A: 20 mM $KH_2PO_4$, pH 4.0; and
buffer B: 20 mM $KH_2PO_4$, 1 M NaCl, pH 4.0.

The fermentation broth of the engineered bacteria was collected, and a ceramic membrane separation system (Jiangsu Jiuwu Hi-Tech Co., Ltd., JWCMF-9) was used to separate bacterial cells and a fermentation supernatant. A cation exchange medium (a chromatography packing was UniGel-80sp produced by Suzhou Nanomicro Technology Co., Ltd., which was loaded in a fully automatic chromatography system produced by Jiangsu Hanbon Science & Technology Co., Ltd.) was equilibrated with buffer A until the A215 absorbance value and conductivity value remained unchanged, and then a sample was loaded at a flow rate of 100 us/cm and a volume of 20 L/time; and the UV A215 absorbance was detected, and when it increased, the collection of an effluent was started. When the sample loading was completed, the collection of effluent was stopped, and then the cation exchange medium was equilibrated with buffer A; when the A215 absorbance decreased, the collection of effluent was started; and when the UV absorbance and conductivity dropped to the minimum and no longer changed, the collection of effluent was stopped. Elution was conducted with each of 500 mM and 1 M sodium chloride, and an eluate was collected. The purified protein in each of the 500 mM eluate and 1 M eluate was detected, then each of the eluate was subjected to dialysis (with ultrapure water (UPW) as a dialysis soution), concentration, and lyophilization, and the resulting lyophilized collagen sponge was collected.

The lyophilized collagen sponges (170801 and 170802) were each dissolved with UPW to 2 mg/mL, the resulting solution was filtered through a 0.22 μm filter membrane, and 10 μL of the solution was taken and injected into a Sepax Bio-C18 chromatographic column (HPLC Waters2695 or Agilent LC1260) to analyze a purity of each of the purified collagens 170801 and 170802.

Figure 13:
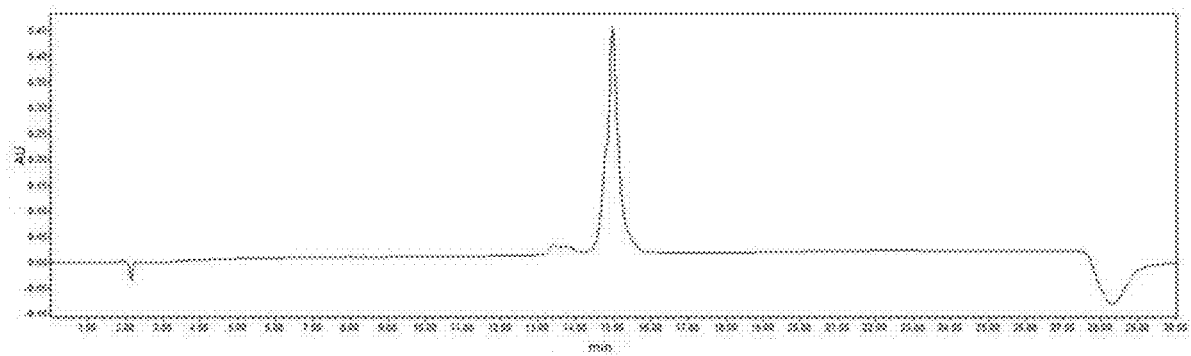
FIG. 13 shows a high-performance liquid chromatography (HPLC) spectrum of the purified collagen 170801.
Figure 14:
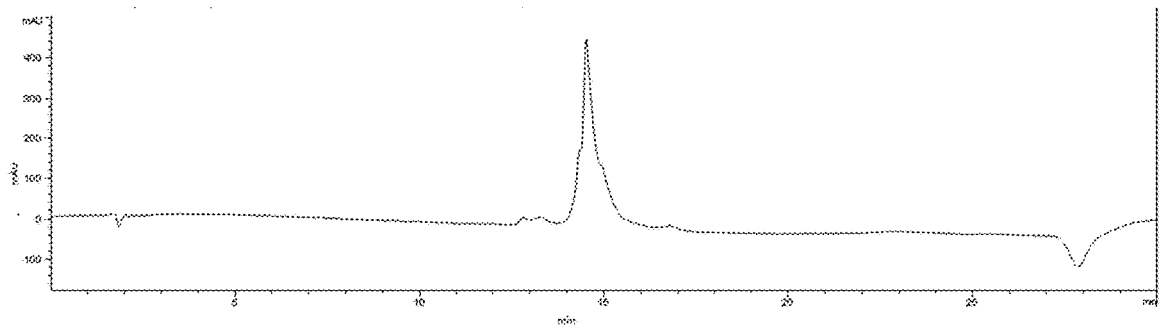
FIG. 14 shows an HPLC spectrum of the purified collagen 170802.

The purification results were shown in FIG. 13 and FIG. 14, and it can be seen that the purified collagens 170801 and 170802 had obvious single peaks and high purities (91.2% and 90%), indicating that the purification method of the present disclosure is reliable and effective and the obtained collagens have a high purity.

In addition to the purification method used in this example, since the collagens 170801 and 170802 each have a Strep-Tag II at the amino terminus and a hexahistidine tag at the carboxyl terminus, Ni-NTA, Strep-Tactin, and other affinity media can be used for single or dual affinity purification, which can also achieve a similar effect to this example.

(3) Characterization of Properties of the Recombinant Collagens

Figure 15:
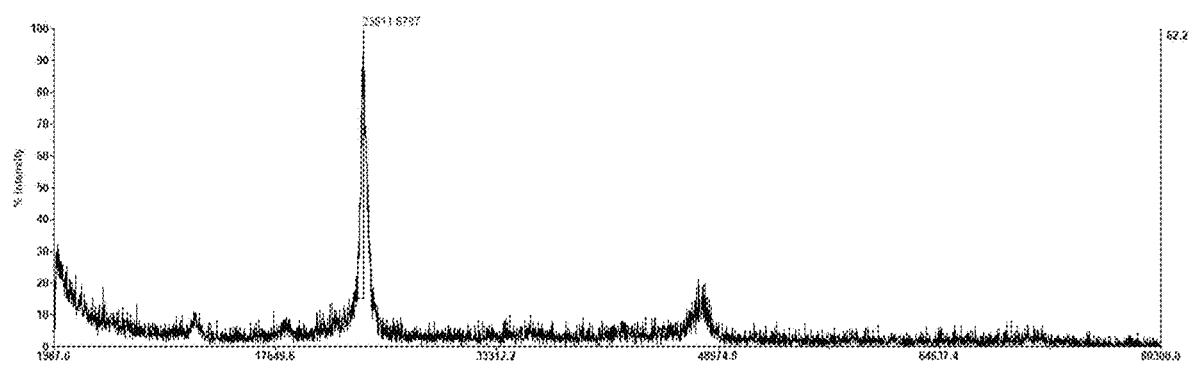
FIG. 15 shows an MALDI-TOF MS result of a molecular weight of the collagen 170801.
Figure 16:
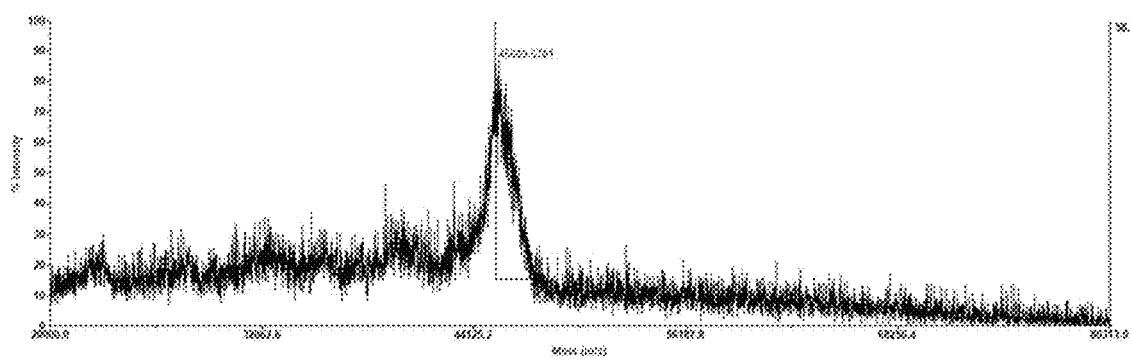
FIG. 16 shows an MALDI-TOF MS result of a molecular weight of the collagen 170802.

Molecular Weight Determination:

The theoretically-predicted molecular weights of the obtained proteins 170801 and 170802 were 23.8 kDa and 45.4 kDa, respectively, and the AMWs detected by SDS-PAGE were larger than the theoretically-predicted values. The lyophilized products of the recombinant human type XVII collagens 170801 and 170802 purified were each subjected to MALDI-TOF MS (AB SCIEX 5800 MALDI-TOF/TOF) to detect their relative molecular weights and determine their actual protein molecular weights, which was entrusted to Sangon Biotech (Shanghai) Co., Ltd. The results were shown in FIG. 15 and FIG. 16, and it can be seen that, as detected by MALDI-TOF MS (charge number+1), the collagen 170801 had a molecular weight of 23811.6797 Da (theoretical value: 23800 Da) and the collagen 170802 had a molecular weight of 45689.5781 Da (theoretical value: 45400 Da); and due to the post-translational modification after expression in $P.$ $pastoris$ and the systematic errors in the molecular weight determination, the actually expressed collagen had a molecular weight consistent with the theoretical value.

Fourier Transform Infrared Spectroscopy (FT-IR) Analysis:

The characteristic absorption peaks of groups in the collagen could be detected by FT-IR analysis. A trace amount of each of the purified lyophilized products of the collagens 170801 and 170802 was taken, ground into a powder with KBr, then pressed into a tablet, and scanned in a range of 4,000 cm$^{-1}$ to 400 cm$^{-1}$ at room temperature (Thermo Scientific, Nicolet™ iS™ 10 FT-IR Spectrometer). The method and result analysis could be found in the literature (Jeong, H., J. Venkatesan and S. Kim, Isolation and characterization of collagen from marine fish (Thunnus obesus). Biotechnology and Bioprocess Engineering, 2013. 18(6): p. 1185-1191.)

Figure 17:
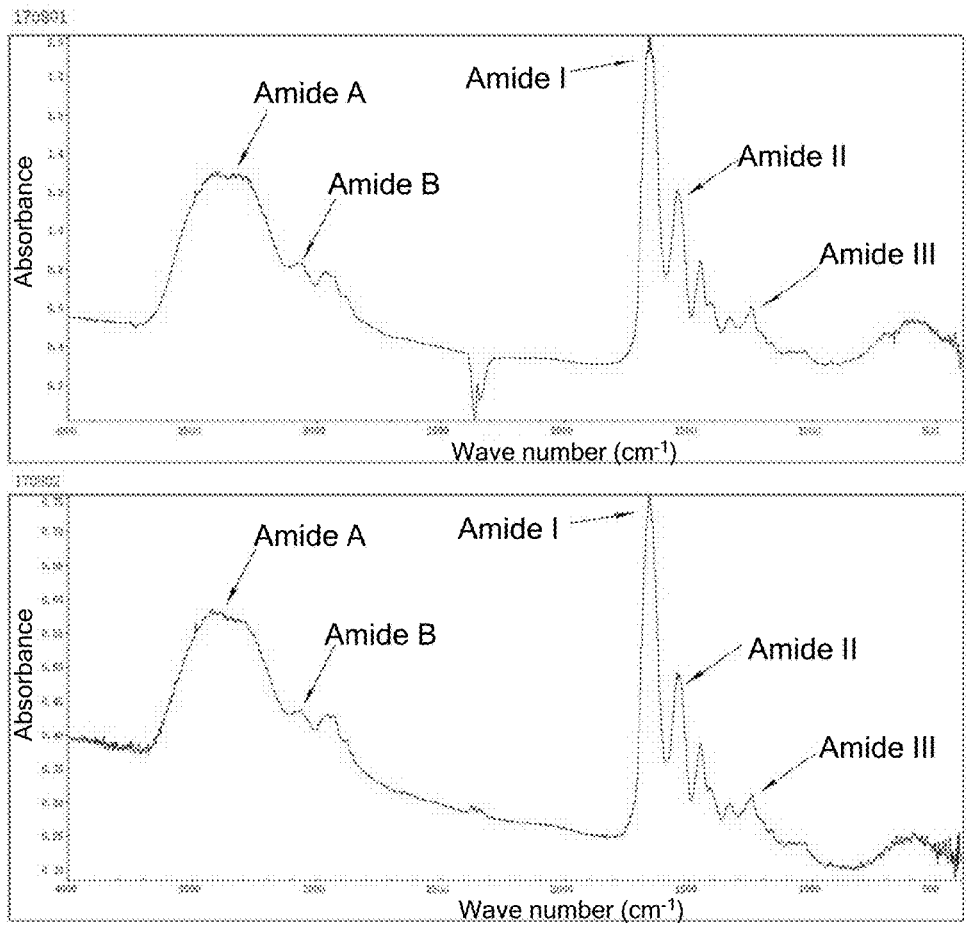
FIGS. 17A-17B show IR spectra of the purified collagens 170801 and 170802.

From the IR spectra of the purified samples of collagens 170801 and 170802 in FIGS. 17A-17B, it can be seen that wave numbers of amide A, amide B, amide I, amide II, and amide III were all in line with the structural characteristics of recombinant collagen (as shown in literatures [1]. Chen Jingtao et al., Infrared Spectroscopy of Recombinant Collagen and Bovine Type I Collagen. Materials Reports, 2008 (03): p. 119-121; [2]. Doyle, B. B., E. G. Bendit and E. R. Blout, Infrared spectroscopy of collagen and collagen-like polypeptides. Biopolymers, 1975. 14 (5): p. 937-957; and [3]. Zhou Aimei et al., Isolation, Purification, and Structural Characterization of Recombinant Human Collagen. Food and Fermentation Industries, 2015 (03): p. 46-52.).

Figure 18:
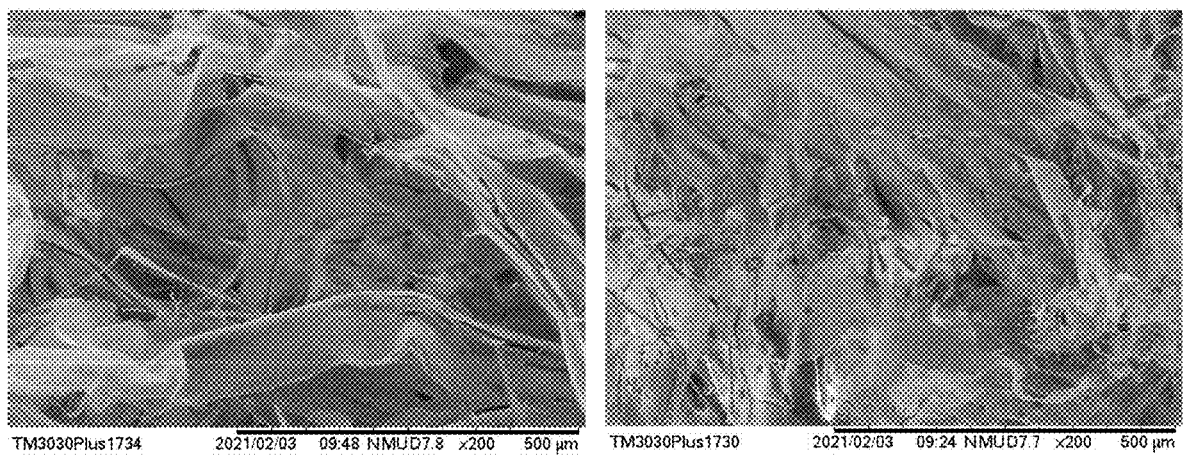
FIGS. 18A-18B show scanning electron microscopy (SEM) images (200×) of lyophilized collagen sponge samples: 170801 (left) and 170802 (right).

SEM Analysis of Lyophilized Collagen Sponge Samples:

A scanning electron microscope (Hitachi TM3030PLUS) was used to scan a surface of each of the lyophilized collagen sponge samples (170801 and 170802), and results were shown in FIGS. 18A-18B. It can be seen from the figure that the recombinant human type XVII collagens 170801 and 170802 each have an obvious lamellar structure, which is similar to a lamellar distribution of human type XVII collagen on a basement membrane in the human body. Such a structure indicates that the collagens have the potential to be used in the field of biomedical materials.

Example 3: Detection of Cell Adhesion Activity of Recombinant Collagens

A method for detecting the cell adhesion activity of the recombinant collagens can be found in the literature: Juming Yao, Satoshi Yanagisawa, Tetsuo Asakura. Design, Expression and Characterization of Collagen-Like Proteins Based on the Cell Adhesive and Crosslinking Sequences Derived from Native Collagens, J Biochem. 136, 643-649 (2004). The detection of cell adhesion activity was entrusted to the Functional Nanomaterials and Biomedical Testing Laboratory of School of Pharmacy, Changzhou University.

A specific implementation method was as follows:

NIH/3T3 cells purchased from the Cell Bank of the Chinese Academy of Sciences (Item No. GNM6, the cultivation and passage methods were conducted according to instructions of the cells) were cultivated normally. The purified lyophilized protein samples 170801 and 170802, a control sample (native human collagen purchased from Sigma, Item No. C7774), and bovine serum albumin (BSA, purchased from Sangon Biotech (Shanghai) Co., Ltd.) were each taken and dissolved with UPW or a 1 M HCl solution, then a protein concentration was determined according to a UV protein quantification empirical formula of C (mg/mL) $=0.144*(A215-A225)$, and then the resulting solutions were each diluted to 0.5 mg/mL with phosphate buffered saline (PBS) (pH 7.4). 100 μL of each of the protein solutions and blank PBS solution was added to a 96-well cell culture plate, and the plate was allowed to stand for 60 min at room temperature; and then 3T3 cells in a well growth state were added at $10^5$ cells/well, and incubated at 37° C. and 5% $CO_2$ for 60 min. Cells in each well were washed 4 times with PBS. An LDH detection kit (Roche, 04744926001) was used to detect the absorbance $OD_{492nm}$ (specific operations were conducted with reference to instructions).

Figure 19:
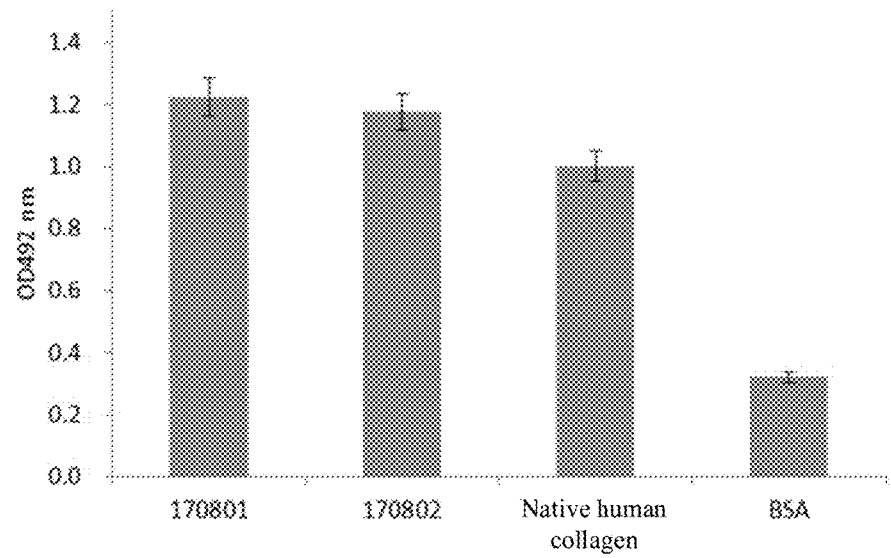
FIG. 19 shows detection results of cell adhesion activity of collagens 170801 and 170802.

The absorbance $OD_{492nm}$ can correspondingly characterize the cell adhesion activity of a collagen sample. The higher the absorbance, the more cells the collagen adheres to and the higher the cell adhesion activity, such that the collagen is more likely to help cells adhere to a wall or adhere to an extracellular matrix in a short time, which is conducive to building an excellent extracellular environment. It can be seen from the results in FIG. 19 that the recombinant human type XVII collagens 170801 and 170802 have higher cell adhesion activity than the commercial native human collagen.

Example 4: Detection of Cell Migration-Promoting Activity of Recombinant Collagens by a Scratch Method A method for detecting and analyzing the cell migration-promoting activity of the recombinant collagens can be found in the literature: Bobadilla, A., et al., In vitro cell migration quantification method for scratch assays. J R Soc Interface, 2019. 16 (151): p. 20180709. The cell migration-promoting activity detection and analysis was entrusted to the Functional Nanomaterials and Biomedical Testing Laboratory of School of Pharmacy, Changzhou University.

A specific implementation method was as follows.

The purified lyophilized collagen samples 170801 and 170802, a control sample (native human collagen purchased from Sigma, Item No. C7774), and BSA (purchased from Sangon Biotech (Shanghai) Co., Ltd.) were each taken and dissolved with UPW or a 1 M HCl solution, then a protein concentration was determined according to a UV protein quantification empirical formula of C (mg/mL)=0.144*(A215-A225), then the resulting solutions were each diluted to 0.5 mg/mL with a DMEM serum-free medium (GIBCO, Item No. 12800017, pH 7.4), and after the dilution, a pH was adjusted to 7.0 to 7.4. NIH/3T3 cells purchased from the Cell Bank of the Chinese Academy of Sciences (Item No. GNM6, the cultivation and passage methods were conducted according to instructions of the cells) were cultivated and passaged normally. Cells in a well growth state were inoculated into a 6-well plate and cultivated for 36 h, where 2 mL of a cell suspension with 20,000 cells/mL was inoculated in each well. A scratch was prepared with a 200 μL pipette tip, and the cells were washed 3 times with PBS to remove the scratched cells. The protein solutions diluted with the DMEM serum-free medium were each added to a well, the cells were further cultivated in a 37° C. and 5% $CO_2$ incubator, and then a sample was collected and photographed at 0 h, 24 h, and 48 h. The Image J software was used to process images of cell migration to obtain the data of initial scratch area and cell-free blank area, and a migration rate was calculated as follows: migration rate=(1−cell-free blank area/initial scratch area)*100%.

Figure 20:
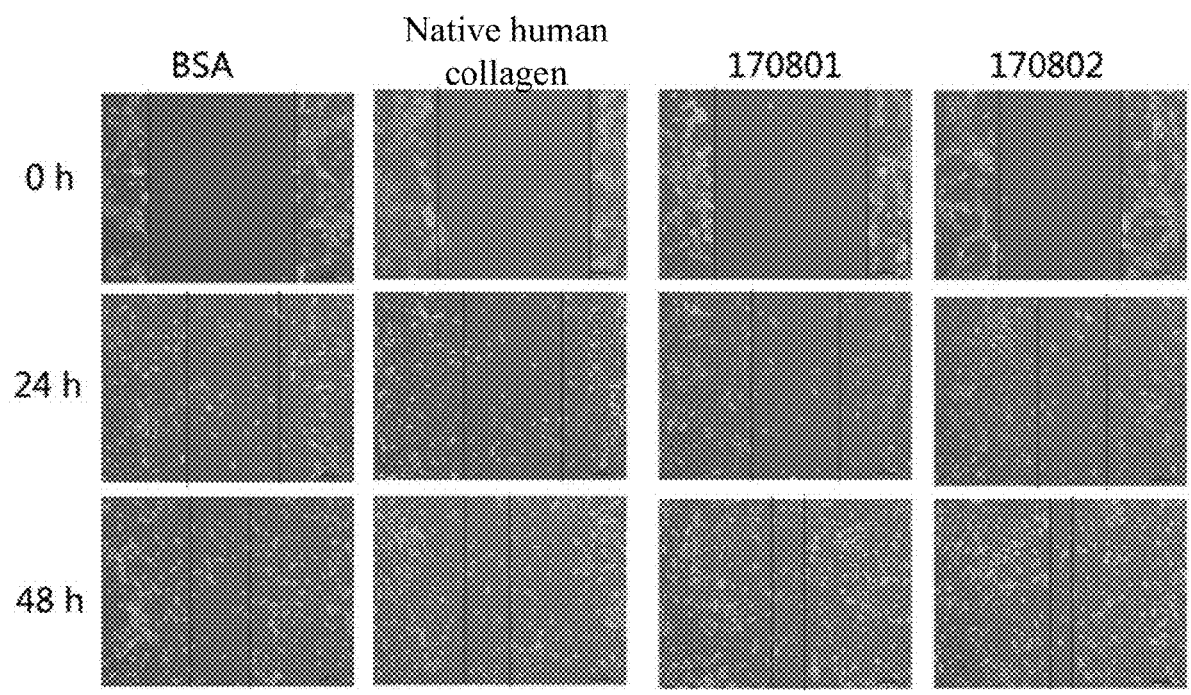
FIG. 20 shows the comparison of actual cell migration in the collagens 170801 and 170802 with the native human collagen.
Figure 21:
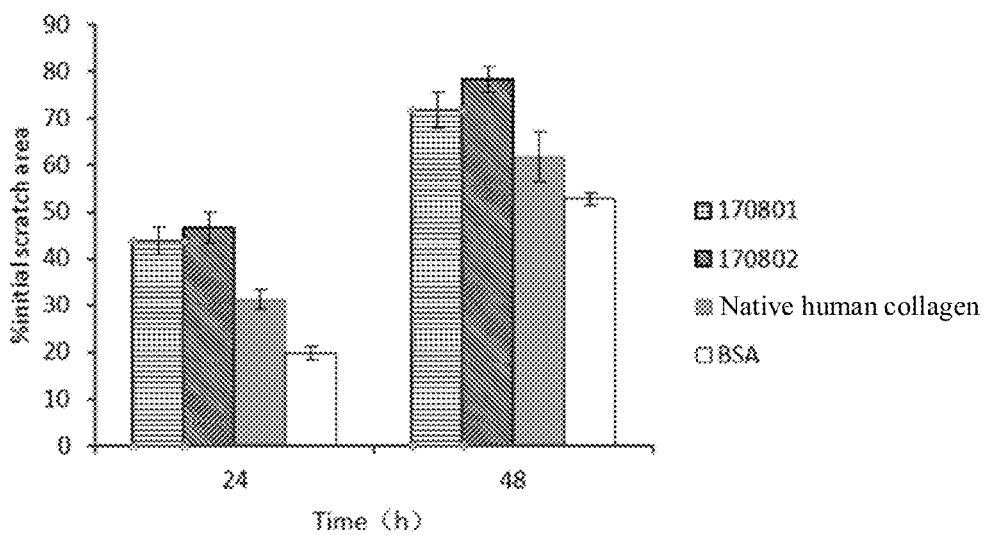
FIG. 21 shows cell migration rates in the collagens 170801 and 170802 as well as the native human collagen after 24 h and 48 h of cell migration.

The in vitro cell migration experiment simulated a process of in vivo cell migration to some extent, and directly reflected an interaction between cells and an extracellular matrix and an interaction between cells under the influence of the matrix. The cell migration-promoting activity is an index to effectively characterize the biological activity of collagen. The higher the migration rate, the higher the biological activity of the collagen. From the comparison of actual cell migration images taken at different time points (areas between two black lines are scratch wound areas at the beginning and after cell migration) in FIG. 20 and the comparison of the calculated cell migration rates shown in FIG. 21 (a cell-free blank area is calculated by Image J), it can be seen that the recombinant human type XVII collagens 170801 and 170802 have higher cell migration-promoting activity than the commercial native human collagen.

Example 5: Preparation of Recombinant Collagen Gels 170801 and 170802 and Rabbit Ear Scar Model Experiment Sodium carboxymethyl cellulose (CMC-Na) and each of purified lyophilized collagen products 170801 and 170802 were separately dissolved in UPW to obtain a 0.01% CMC-Na solution and a 5% collagen solution, and then the 0.01% CMC-Na solution was thoroughly mixed with the 5% collagen solution to prepare a collagen gel. A CMC-Na gel without collagen was adopted as a negative control.

New Zealand white rabbits (purchased from the Experimental Animal Center of the Naval Medical University) each weighing 2 kg to 3 kg were selected and raised in a well-ventilated room at 21° C. for 2 weeks before the experiment to adapt to the environment, with a 12 h day-night cycle and single-cage raising. Subsequently, scar models were constructed: The experimental animals were administered with 30 g/L pentobarbital sodium at 1.0 mL/kg (30 mg/kg) for ear vein anesthesia, and after the anesthesia was achieved, the skin was disinfected with alcohol 3 times. A skin biopsy device with a diameter of 1 cm was used to draw a neat skin incision margin at an inner side of a rabbit ear, and ophthalmic scissors were used to cut a full-thickness skin defect wound with a diameter of about 1 cm, which was exposed to a bone surface of an ear cartilage. The wound was covered with sterile vaseline gauze inside and sterile gauze outside, and then bandaged and fixed. The wound was disinfected and debrided with iodophor and the wound dressing was changed every 2 d to 3 d.

On day 21, after the wound healed, the rabbits were grouped and subjected to a scar intervention treatment. The collagen gels 170801 and 170802 were each applied to the wound in combination with an iodine-containing antibacterial surgical foil (Drape Antimicrob®, Minnesota Mining and Manufacturing Company, USA) and a self-adhesive silicone film dressing (Cica-Care®, Smith & Nephew, England) for scar intervention.

A digital camera and a dermoscope were used to record the scar conditions during the 1-6 week scar intervention experiment. At the 6th week, the rabbits were anesthetized and sacrificed by injecting a supersaturated potassium chloride solution into the ear vein, and ear scar samples were collected, soaked in a fixing solution, subjected to hematoxylin and eosin (HE) staining and MASSON staining, observed under a microscope, and photographed. Specific methods can be found in the following literatures: [1] Liu Tong. Experimental Study on Use of Recombinant Human Collagen Hydrogel and Artificial Dermis as Microskin Graft coverings to Repair Full-Thickness Skin Defects [D]. Naval Medical University, 2019; and [2] Experimental Guidance of Histology and Embryology [M] edited by Li Jicheng, Beijing: People's Medical Publishing House, 2018. 09.

Figure 22:
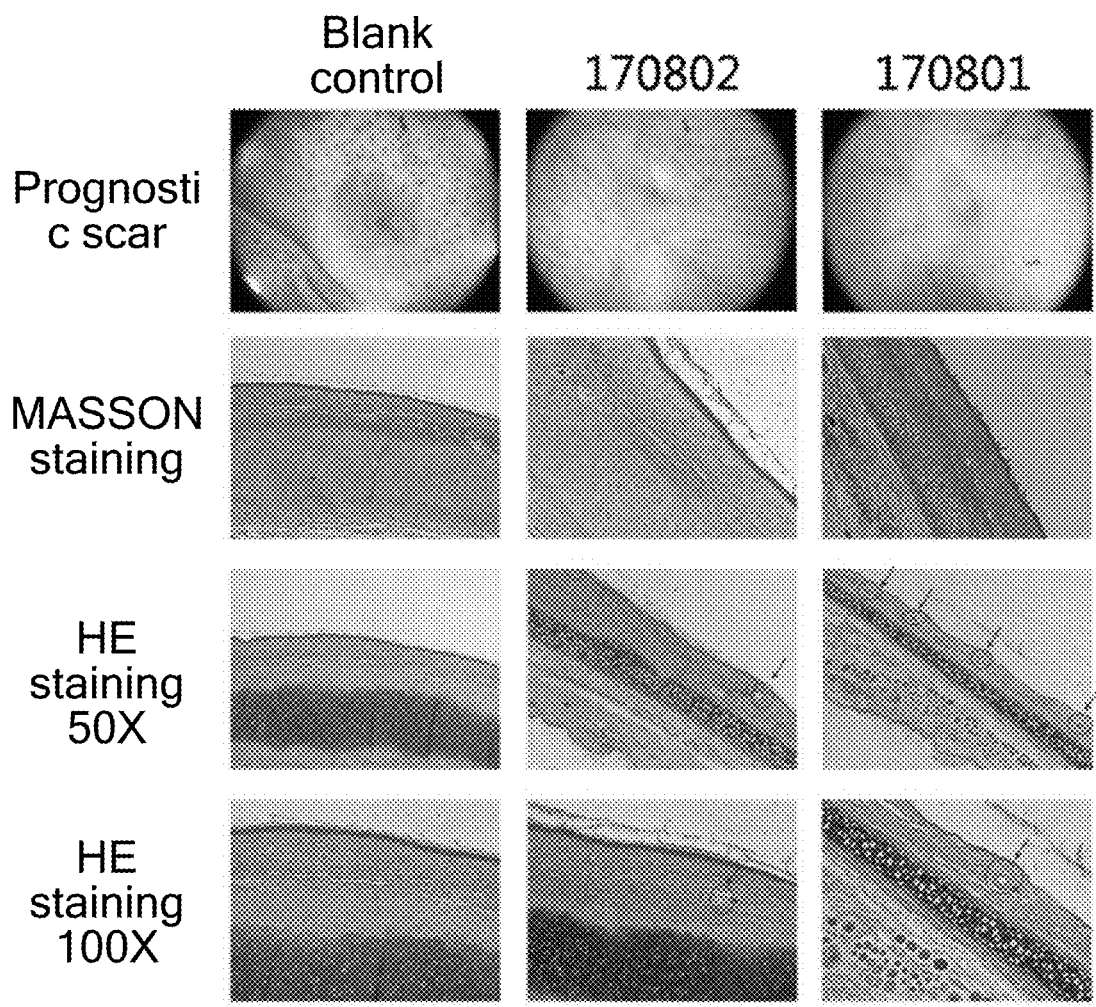
FIG. 22 shows gross images of rabbit ear scars intervened with the collagens 170801 and 170802 for 6 weeks and images of scar sections.

Experimental results were shown in FIG. 22. In the experimental group, after being intervened with the collagen gels 170801 and 170802, the wound at the rabbit ear skin well healed, and there was obvious new hair growth at an inner side of the rabbit ear, indicating that the collagens have obvious biological functions of promoting hair follicle generation and hair growth; and it can be seen from the Masson staining and HE staining results of tissue sections that collagen fibers in the tissue were arranged orderly, a dermal tissue was generated and especially a new hair follicle structure was generated, and there was obviously hair growth (inside a circle indicated by an arrow in the figure), clearly indicating that the collagens have the biological functions to promote dermal tissue repair and hair follicle regeneration (hair generation). In the control group, the prognostic scar still had a large number of regular and dense collagen deposits, which was similar to the scar structure; and no hair follicle structure, no dermal tissue, and no new rabbit hair were generated. The experimental results show that the recombinant human type XVII collagens 170801 and 170802 have excellent biological activities to promote tissue repair and hair follicle repair and regeneration.

What is claimed is:

1. A recombinant human type XVII collagen selected from the group consisting of SEQ ID NO: 2 and SEQ ID NO: 3.

2. The recombinant human type XVII collagen according to claim 1, wherein a Strep-Tag II is added to the amino terminus and a hexahistidine tag is added to the carboxyl terminus of the recombinant human type XVII collagen.

3. The recombinant human type XVII collagen according to claim 1, wherein the recombinant human type XVII collagen according to claim 1 has an activity selected from the group consisting of a cell adhesion activity, a cell migration-promoting activity, a tissue regeneration-promoting activity, and a hair follicle repair and regeneration-promoting activity.

4. A composition comprising the recombinant human type XVII collagen according to claim 1.

5. An article comprising the recombinant human type XVII collagen according to claim 1 or a composition comprising the recombinant human type XVII collagen according to claim 1, wherein the article is selected from the group consisting of a drug, a medical device, a biological material, a tissue-engineered product, a cosmetic, and a health product.

6. A preparation method of the recombinant human type XVII collagen according to claim 1, comprising the following steps:
  (1) constructing an engineered bacteria that expresses an amino acid sequence selected from the group consisting of SEQ ID NO: 2 and SEQ ID NO: 3;
  (2) screening the engineered bacteria of step (1) for high expression of the recombinant human type XVII collagen according to claim 1;
  (3) fermenting the engineered bacterium of step (2) in a fermentation tank thereby obtaining a fermentation supernatant comprising the recombinant human type XVII collagen according to claim 1; and
  (4) purifying the fermentation supernatant of step (3) and obtaining high-purity recombinant human type XVII collagen according to claim 1.

7. The preparation method according to claim 6, wherein the engineered bacterium with the high expression screened out in step (1) is *Pichia pastoris* with an accession number of CGMCC 20626 or CGMCC 20627.

8. A method for manufacture of a product comprising the step of adding the recombinant human type XVII collagen according to claim 1 to a product, wherein the product is selected from the group consisting of a drug, a medical device, a biological material, a tissue-engineered product, a cosmetic, and a health product.

9. A method for manufacture of a product comprising the step of adding the recombinant human type XVII collagen according to claim 1 to a product for promoting scar healing, tissue repair, or hair follicle repair.

10. The method according to claim 9, wherein the product is an external preparation.

11. The method according to claim 10, wherein the product is the external preparation for a topical application.

12. The method according to claim 11, wherein the product is an external gel for the topical application.

13. A polynucleotide encoding a recombinant human type XVII collagen selected from the group consisting of SEQ ID NO: 2 and SEQ ID NO: 3.

14. The polynucleotide according to claim 13, wherein the polynucleotide is selected from the group consisting of SEQ ID NO: 6 and SEQ ID NO: 7.

15. A method for manufacture of a product comprising the step of expressing the polynucleotide according to claim 13 in a product, wherein the product is selected from the group consisting of a drug, a medical device, a biological material, a tissue-engineered product, a cosmetic, and a health product.

16. The method according to claim 15, wherein the polynucleotide has a nucleotide sequence selected from the group consisting of SEQ ID NO: 6 and SEQ ID NO: 7.

17. A method for manufacture of a product comprising the step of expressing the polynucleotide according to claim 13 in a product for promoting scar healing, tissue repair, or hair follicle repair.

18. The method according to claim 17, wherein the polynucleotide has a nucleotide sequence selected from the group consisting of SEQ ID NO: 6 and SEQ ID NO: 7.

19. A recombinant expression vector carrying the polynucleotide according to claim 13.

20. An engineered bacterium carrying the recombinant expression vector according to claim 19.

21. The engineered bacterium according to claim 20, wherein the engineered bacterium is *Pichia pastoris*.

22. A cell carrying the recombinant expression vector according to claim 19.

23. The cell according to claim 22, wherein the cell is *Pichia pastoris*.

24. The recombinant expression vector according to claim 19, wherein the polynucleotide has a nucleotide sequence selected from the group consisting of SEQ ID NO: 6 and SEQ ID NO: 7.

25. A method for manufacture of a product comprising the step of expressing the recombinant expression vector according to claim 19 in a product, wherein the product is selected from the group consisting of a drug, a medical device, a biological material, a tissue-engineered product, a cosmetic, and a health product.

26. A method for manufacture of a product comprising the step of expressing the recombinant expression vector according to claim 19 in a product for promoting scar healing, tissue repair, or hair follicle repair.

27. A method for manufacture of a product comprising the step of fermenting the engineered bacterium according to claim 20 to produce a product, wherein the product is selected from the group consisting of a drug, a medical device, a biological material, a tissue-engineered product, a cosmetic, and a health product.

28. A method for manufacture of a product comprising the step of fermenting the engineered bacterium according to claim 20 to produce a product for promoting scar healing, tissue repair, or hair follicle repair.

29. A method for manufacture of a product comprising the step of adding the composition according to claim 4 to a product, wherein the product is selected from the group consisting of a drug, a medical device, a biological material, a tissue-engineered product, a cosmetic, and a health product.

30. A method for manufacture of a product comprising the step of adding the composition according to claim 4 to a product for promoting scar healing, tissue repair, or hair follicle repair.

* * * * *